United States Patent
Naylor et al.

[11] Patent Number: 5,935,972
[45] Date of Patent: Aug. 10, 1999

[54] BENZOFURAN DERIVATIVES AS TACHYKININ ANTAGONISTS

[75] Inventors: Alan Naylor; Brian Evans, both of Stevenage, United Kingdom

[73] Assignee: Glaxo Group Limited, United Kingdom

[21] Appl. No.: 08/793,099

[22] PCT Filed: Aug. 25, 1994

[86] PCT No.: PCT/EP94/02804

§ 371 Date: May 14, 1997

§ 102(e) Date: May 14, 1997

[87] PCT Pub. No.: WO95/06645

PCT Pub. Date: Mar. 9, 1995

[51] Int. Cl.$^6$ .................. A61K 31/445; C07D 405/14
[52] U.S. Cl. ............................ 514/320; 546/196
[58] Field of Search ............... 514/320; 546/196

[56] References Cited

U.S. PATENT DOCUMENTS

| | | | |
|---|---|---|---|
| 5,332,817 | 7/1994 | Desai et al. | 546/16 |
| 5,364,943 | 11/1994 | Rosen et al. | 546/223 |

FOREIGN PATENT DOCUMENTS

| | | |
|---|---|---|
| 0 124 783 | 11/1984 | European Pat. Off. . |
| 93 01170 | 1/1993 | WIPO . |
| 93 11110 | 6/1993 | WIPO . |
| WO94/04496 | 3/1994 | WIPO . |
| 95/08549 | 3/1995 | WIPO . |
| 96/20009 | 7/1996 | WIPO . |

OTHER PUBLICATIONS

Maggi et al. "Tachykinin receptors and tachykinin receptor antagonists" J. Auton. Pharmac. v.13, pp. 23–24, 1993.
Tavorath et al. "Drug treatment of chemotherapy induced delayed emesis" MEDLINE abst. 97–081298, 1997.
Tattersall et al. "Tachykinin NK1 receptor antagonists act centrally to inhibit emesis induced by the chemotherapeutic agent cisplatin in ferrets" MEDLINE abst 97–165756, 1997.

*Primary Examiner*—Ceila Chang
*Attorney, Agent, or Firm*—Bacon & Thomas

[57] ABSTRACT

The present invention relates to benzofuran derivatives of formula (I) as shown below.

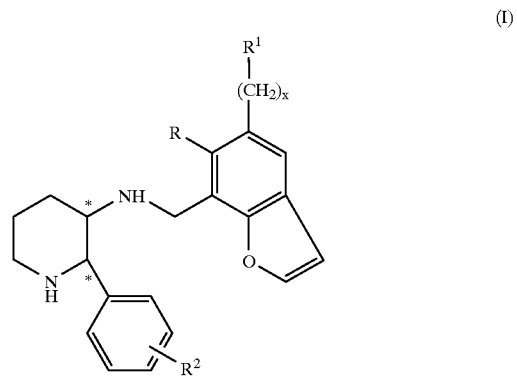

The invention also relates to pharmaceutically acceptable salts and solvates of the derivatives of formula (I) as well as to processes for their preparation and to their use in the treatment of conditions mediated by tachykinins.

13 Claims, No Drawings

BENZOFURAN DERIVATIVES AS TACHYKININ ANTAGONISTS

This application is a 371 of PCT/EP94/02804 filed Aug. 25, 1994.

The present invention relates to benzofuran derivatives, to processes for their preparation, pharmaceutical compositions containing them and their medical use.

In particular the invention relates to novel compounds which are potent and specific antagonists of tachykinins, including substance P and other neurokinins.

3-Aminopiperidine derivatives described as having substance P antagonist activity are disclosed in, for example, PCT Patent Applications WO-A-9109844 and WO-A-9301170.

The present invention provides compounds of formula (I)

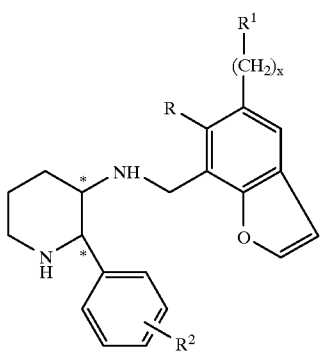

(I)

wherein
R represents a hydrogen atom or a $C_{1-4}$alkoxy group; $R^1$ is selected from phenyl, opitionally substituted by a group —$(CH_2)_n CONR^3 R^4$ or $S(O)_m R^3$; or a 5- or 6-membered aromatic heterocycle containing 1, 2, 3, or 4 heteroatoms selected from oxygen, nitrogen or sulphur, optionally substituted by a $C_{1-4}$alkyl, trifluoromethyl or cyano group or a group —$(CH_2)_n CONR^3 R^4$;
$R^2$ represents a hydrogen or halogen atom;
$R^3$ and $R^4$ independently represent hydrogen or $C_{1-4}$alkyl;
n represents zero, 1 or 2;
m represents zero 1 or 2;
x represents zero or 1;
and pharmaceutically acceptable salts and solvates thereof.

Suitable pharmaceutically acceptable salts of the compounds of general formula (I) include acid addition salts formed with pharmaceutically acceptable organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates.

Other acids, such as oxalic, while not in themselves pharmaceutically acceptable, may be useful in the preparation of salts useful as intermediates in obtaining the compounds of formula (I) and their pharmaceutically acceptable acid addition salts.

The solvates may, for example, be hydrates.

References hereinafter to a compound according to the invention includes both compounds of formula (I) and their pharmaceutically acceptable acid addition salts together with pharmaceutically acceptable solvates.

It will be appreciated by those skilled in the art that the compounds of formula (I) contain at least two chiral centers (shown as * in formula (I)) and thus exist in the form of two pairs of optical isomers (i.e. enantiomers) and mixtures thereof including racemic mixtures.

For example the compounds of formula (I) may be either cis isomers, as represented by figures (a) and (b), or trans isomers, as represented by figures (c) and (d), or mixtures thereof.

All of the isomers of the compounds of formula (I) represented by the figures (a) to (d) and mixtures thereof including racemic mixtures are included within the scope of the invention.

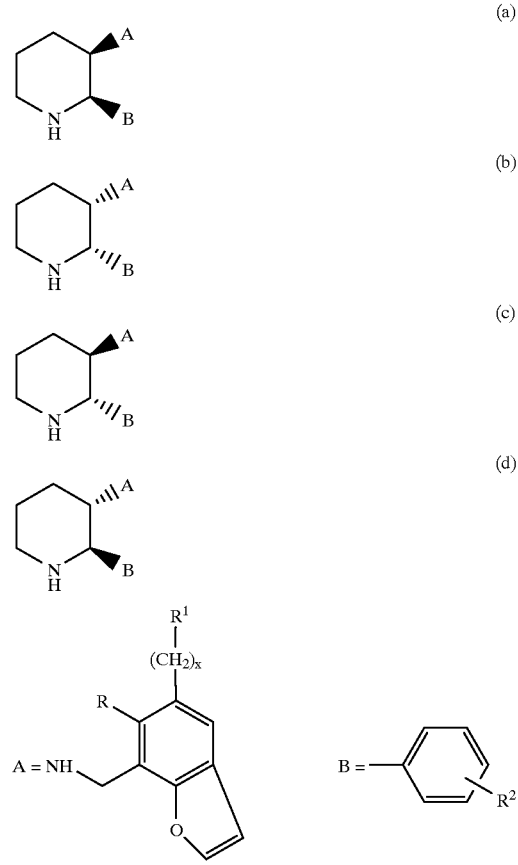

The compounds of formula (I) are preferably in the form of their cis isomers (i.e. as represented by figures (a) and (b)). The 2S, 3S isomers (i.e. as represented by figure (b)) are particularly preferred.

According to a further aspect the invention provides compounds of formula (I) wherein R represents a hydrogen atom, $R^1$ is selected from phenyl, optionally substitued by a group —$(CH_2)_n CONR^3 R^4$ or $S(O)_m R^3$; or a 5- or 6-membered aromatic heterocycle containing 1,2,3, or 4 heteroatoms selected form oxygen, nitrogen or sulphur, optionally substituted by a $C_{1-4}$alkyl group; $R^2$ represents a hydrogen atom; $R^3$ and $R^4$ independently represent hydrogen or $C_{1-4}$alkyl; n represents zero, 1 or 2; m represents 1 or 2; and x represents zero.

Referring to the general formula (I), a 5- or 6-membered aromatic heterocycle containing 1, 2, 3 or 4 heteroatoms selected from oxygen, nitrogen or sulphur may be, for example pyrimidine, furan, pyridine, imidazole, tetrazole, pyrazole, pyrazine, oxazole, thiazole, triazole such as 1,2, 4-triazole or 1,2,3-triazole, isoxazole, 1,2,4-oxadiazole or 1,3,4-oxadiazole.

Preferred 5- or 6-membered aromatic heterocycles containing 1,2,3 or 4 heteroatoms selected from oxygen, nitrogen or sulphur include pyrimidine, furan, pyridine, imidazole, tetrazole, pyrazole, pyrazine, oxazole, thiazole, 1,2,4-triazole, 1,2,3-triazole and isoxazole. Further preferred groups include pyrimidine, furan and pyridine, especially pyridine. Even further preferred are 1,2,3-triazole, 1, 2, 4-triazole and tetrazole, especially tetrazole.

Referring to the general formula (I), when $R^1$ represents a heterocyclic group as defined above, this may be attached to the remainder of the molecule via any vacant carbon or nitrogen atom of the heterocycle. For example, when $R^1$ represents pyrimidine, the pyrimidine ring may be attached via the 5-position, when $R^1$ represents furan, the furan ring may be attached via the 3-position, when $R^1$ represents pyridine, the pyridine ring may be attached via the 2-, 3- or 4-position, preferably the 4-position, when $R^1$ represents imidazole, the imidazole ring may be attached via the 1-, 2- or 4-position, when $R^1$ represents pyrazole, the pyrazole ring may be attached via the 1-, 3- or 4-position, when $R^1$ represents pyrazine, the pyrazine ring may be attached via the 2-position, when $R^1$ represents oxazole, the oxazole ring may be attached via the 2-position, when $R^1$ represents thiazole, the thiazole ring may be attached via the 2-position, when $R^1$ represents isoxazole, the isoxazole ring may be attached via the 4-position, when $R^1$ represents tetrazole, the tetrazole ring may be attached via the 1-, 2- or 5-position, when $R^1$ represents 1, 2, 3-triazole, the 1, 2, 3-triazole ring may be attached via the 1-, 4- or 5-position, when $R^1$ represents 1, 2, 4-triazole, the 1, 2, 4-triazole ring may be attached via the 1-, or 3-position.

Referring to the general formula (I), a $C_{1-4}$alkyl group may be a straight chain or branched chain alkyl group and may be, for example, methyl, ethyl, propyl, prop-2-yl, butyl, but-2-yl, 2-methylprop-1-yl or 2-methylprop-2-yl. A halogen atom may be a fluorine, chlorine, bromine or iodine atom. $R^2$ is suitably a fluorine atom, for example a fluorine atom in the meta or preferably the para position.

Referring to the general formula (I), when the phenyl or above defined heterocycle is substituted, there may be one or two substituents which may be present at any vacant position on the phenyl or heterocyclic ring. A suitable substituent for the phenyl ring includes $SO_2Me$. Suitable substituents for the heterocycle include methyl, cyano, trifluoromethyl or $CONMe_2$. For example, when $R^1$ in the general formula (I) represents a pyridine ring suitable substituents include cyano, methyl or $CONMe_2$, when $R^1$ represents tetrazole suitable substituents include methyl or trifluoromethyl, when $R^1$ represents imidazole, pyrazole, 1,2,3-triazole, 1,2, 4-trizole or isoxazole suitable substituents include methyl. When $R^1$ represents imidazole, isoxazole or pyrazole, one or two substituents are suitably present, such as one or two methyl groups.

Referring to the general formula (I), n is preferably zero. Referring to the general formula (I), m is preferably zero. Referring to the general formula (I), when $R^1$ represents tetrazole or pyridine, x may represent zero or 1. x preferably represents zero.

Referring to the general formula (I), when $R^1$ represents a substituted phenyl group, the substituent is suitably in the para position and is suitably an $SO_2Me$ group.

When $R^1$ is a substituted triazole ring, the substituent is suitably a methyl group.

Referring to the general formula (I), when $R^1$ represents other than a tetrazole or pyrazole ring, $R^2$ is suitably hydrogen.

Referring to the general formula (I), R is suitably methoxy or, preferably a hydrogen atom. When R is methoxy, $R^1$ is suitably pyridine or pyrazole.

According to one aspect of the invention $R^1$ is preferably a heterocyclic group as defined above, for example an unsubstituted heterocyclic group, such as unsubstituted pyrimidine, furan and pyridine, especially pyridine.

According to a further aspect of the invention a preferred class of compounds of formula (I) are those wherein R is a hydrogen atom, $R^1$ is a triazole ring, such as a 1,2,3-triazole for example attached via the 1-,4- or 5-position, or a 1,2,4-triazole for example attached via the 1- or 3-position, optionally substituted by a methyl group, x is zero and $R^2$ is hydrogen.

Referring to the general formula (I), when $R^1$ represents a tetrazole ring, $R^2$ is suitably a fluorine atom, such as a fluorine atom in the meta or preferably the para position, or preferably $R^2$ is hydrogen. When $R^1$ is a substituted tetrazole ring, the substituent is suitably trifluoromethyl or preferably a methyl group. When $R^1$ is a tetrazole ring attached to the rest of the molecule via the 1-position, the substituent, if present, is suitably attached to the 5-position of the tetrazole ring. When $R^1$ is a tetrazole ring attached to the rest of the molecule via the 5-position, the substituent, if present, is suitably attached to the 1-position of the tetrazole ring. When $R^1$ is a tetrazole ring attached to the rest of the molecule via the 2-position, the tetrazole ring is preferably unsubstituted and x is 1.

According to a yet further aspect of the invention, referring to the general formula (I), when $R^1$ represents a heterocycle as defined above, the heterocycle is preferably a tetrazole ring, more preferably a tetrazole ring substituted with a methyl group. $R^1$ is preferably a tetrazole ring attached directly (i.e. x is zero) to the 5-position of the benzofuran ring via a nitrogen atom, such as via the nitrogen atom in the 1-position. $R^1$ is preferably such an N-linked tetrazole ring substituted on the vacant carbon atom, i.e. the 5-position, by a methyl group.

A preferred class of compounds of formula (I) are those wherein R is a hydrogen atom, $R^1$ is a tetrazole ring, preferably substituted with a trifluoromethyl or more preferably a methyl group, preferably a N-linked tetrazole ring, preferably linked via the nitrogen atom in the 1-position, preferably an N-linked tetrazole ring substituted with a methyl group, the methyl group preferably being attached to the vacant carbon atom, i.e. in the 5-position, x is zero and $R^2$ is a fluorine atom, such as a fluorine atom in the meta or preferably the para position, or more preferably $R^2$ is a hydrogen atom.

Suitable compounds according to the invention are:
cis-(2-Phenyl-piperidin-3-yl)-(5-pyridin-4-yl-benzofuran-7-ylmethyl)-amine;

cis-(2-Phenyl-piperidin-3-yl)-(5-furan-3-yl-benzofuran-7-ylmethyl)-amine;
cis-(2-Phenyl-piperidin-3-yl)-(5-pyrimidin-5-yl-benzofuran-7-ylmethyl)-amine;
and pharmaceutically acceptable salts and solvates thereof.

Also suitable are:
cis-(2-Phenyl-piperidin-3-yl)-(5-pyridin-3-yl-benzofuran-7-ylmethyl)-amine;
cis-(2-Phenyl-piperidin-3-yl)-(5-pyridin-2-yl-benzofuran-7-ylmethyl)-amine;

Further compounds are:
[2S-(4-Fluoro-phenyl)-piperidin-3S-yl]-[5-(2-methyl-2H-pyrazol-3-yl)-benzofuran-7-ylmethyl]-amine;
5-(2,3-Dimethyl-3H-imidazol-4-yl)-benzofuran-7-ylmethyl]-(2S-phenyl-piperidin-3S-yl)-amine;
[5-(3,5-Dimethyl-isoxazol-4-yl)-benzofuran-7-ylmethyl]-[2S-phenyl-piperidin-3S-yl]-amine;
[5-(1-Methyl-1H-imidazol-2-yl)-benzofuran-7-ylmethyl]-(2S-phenyl-piperidin-3S-yl)-amine;
[5-(2-Methyl-2H-pyrazol-3-yl)-benzofuran-7-ylmethyl]-(2S-phenyl-piperidin-3S-yl)-amine;
(2S-Phenyl-piperidin-3S-yl)-[5-(1H-pyrazol-4-yl)-benzofuran-7-ylmethyl]-amine;
cis-(2-Phenyl-piperidin-3-yl)-(5-pyrazin-2-yl-benzofuran-7-ylmethyl)-amine;
4-{7-[(2S-Phenyl-piperdin-3S-ylamino)-methyl]-benzofuran-5-yl}-pyridine-2-carboxylic acid dimethylamide;
4-{7-[(2S-Phenyl-piperidin-3S-ylamino)-methyl]-benzofuran-5-yl}-pyridine-2-carbonitrile;
(2S-Phenyl-piperidin-3S-yl)-(5-pyridin-4-ylmethyl-benzofuran-7-ylmethyl)-amine;
[5-(2-Methyl-pyridin-4-yl)-benzofuran-7-ylmethyl]-(2S-phenyl-piperidin-3S-yl)-amine;
[6-Methoxy-5-pyridin-4-ylbenzofuran-7-ylmethyl]-(2S-phenyl-piperidin-3S-yl)-amine;
[6-Methoxy-5-(2-methyl-2H-pyrazol-3-yl)-benzofuran-7-ylmethyl]-(2S-phenyl-piperidin-3S-yl)-amine;
(5-Isoxazol-4-yl-benzofuran-7-ylmethyl)-(2S-phenyl-piperidin-3S-yl)-amine;
(2S-Phenyl-piperidine-3S-yl)-(5-tetrazol-2-ylmethyl-benzofuran-7-yl-methyl)-amine;
(2S-Phenyl-piperidin-3S-yl)-(5-tetrazol-1-ylmethyl-benzofuran-7-yl-methyl)-amine;
[5-(3,5-Dimethyl-1H-pyrazol-4yl)-benzofuran-7-ylmethyl]-(2S-phenyl-piperidin-3S-yl)amine;
[5-(3-Methyl-3H-imidazol-4-yl)-benzofuran-7ylmethyl]-(2S-phenyl-piperidin-3S-yl)-amine;
(5-Oxazol-2-yl-benzofuran-7-ylmethyl)-(2S-Phenyl-piperidine-3S-yl)-amine;
cis-(2-Phenyl-piperidin-3-yl)-(5-thiazol-2-yl-benzofuran-7-yl-methyl)-amine;
(5-Pyrazol-1-yl-benzofuran-7-ylmethyl)-(2S-phenyl-piperidin-3S-yl)-amine;
(5-Imidazol-1yl-benzofuran-7-ylmethyl)-(2S-phenyl-piperidin-3S-yl)-amine;
and pharmaceutically acceptable salts and solvates thereof.

Preferred compounds according to the invention are:
[5-(1-Methyl-1H-[1,2,3]triazol-5-yl)-benzofuran-7-ylmethyl]-(2S-phenyl-piperidin-3S-yl)-amine;
(2S-Phenyl-piperidin-3S-yl)-(5-tetrazol-1-yl-benzofuran-7-ylmethyl)-amine;
(2S-Phenyl-piperidin-3S-yl)-[5-(2H-[1,2,3]triazol-4-yl)-benzofuran-7-ylmethyl]-amine;
[5-(2-Methyl-2H-[1,2,4]triazol-3-yl)-benzofuran-7-ylmethyl]-[(2S,3S)-phenyl-piperidin-3-yl]-amine;,
[5-(1-Methyl-1H-[1,2,3]triazol-4-yl)-benzofuran-7ylmethyl]-[(2S,3S)-2-phenyl-piperidin-3-yl]-amine;
cis[5-(4-Methanesulfonyl-phenyl)-benzofuran-7-ylmethyl]-2-phenyl-piperidin-3-yl)amine;
[5-(1-Methyl-1H-tetrazol-5-yl)-benzofuran-7-ylmethyl]-(2S-phenyl-piperidine-3S-yl)-amine;
(5-Phenyl-benzofuran-7-ylmethyl)-(2S-phenyl-piperidin-3S-yl)-amine;
(2S-Phenyl-piperidine-3S-yl)-(5-[1,2,3]triazol-1-yl-benzofuran-7-ylmethyl)-amine;
(2S-Phenyl-piperidine-3S-yl)-[5-(5-trifluoromethyl-tetrazol-1-yl)-benzofuran-7-yl-methyl]-amine;
(2S-Phenyl-piperidin-3S-yl)-(5-[1,2,4]triazol-1-yl-benzofuran-7-ylmethyl)-amine;
[5-(5-Methyl-tetrazol-1-yl)-benzofuran-7-ylmethyl]-[2S-(4-fluoro-phenyl)-piperidin-3S-yl]-amine;
and pharmaceutically acceptable salts and solvates thereof.

A particularly preferred compound according to the invention is [5-(5-Methyl-tetrazol-1-yl)-benzofuran-7-ylmethyl]-(2S-phenyl-piperidin-3S-yl)-amine and pharmaceutically acceptable salts and solvates thereof.

The compounds of the invention are antagonists of tachykinins, including substance P and other neurokinins both in vitro and in vivo and are thus of use in the treatment of conditions mediated by tachykinins, including substance P and other neurokinins.

The compounds of the invention possess $NK_1$-receptor binding affinity as determined in vitro by their ability to displace [3H]-substance P (SP) from $NK_1$ receptors in cell membranes of U-373MG human astrocytoma cells. U-373MG membranes (25–35 μg protein per tube) were prepared and incubated with [3H]-SP (0.6–0.8 nM) at 20° C. for 40 min. Non-specific binding was defined as that remaining in the presence of 1 μM (+) CP-99,994.

$NK_1$-receptor binding affinity has also been determined in vitro by the compounds' ability to displace [3H]-substance P (SP) from recombinant human $NK_1$ receptors expressed in Chinese Hamster Ovary (CHO) cell membranes. CHO membranes (3–5 μg protein per tube) were prepared and incubated with [3H]-SP (0.6–0.8 nM) at 20° C. for 40 min. Non-specific binding was defined as that remaining in the presence of 1 μM (+) CP99,994.

The compounds of the invention have been shown to have anti-emetic activity as indicated by for example their ability to inhibit radiation-induced emesis in the ferret. In this model of emesis the onset of retching and vomiting occurs approximately 20 minutes after whole body irradiation (2 Grey≡200 Rads). The test compound is administered (e.g. i.p, p.o., i.v., s.c) immediately after irradiation and its effect on emesis determined by comparison with appropriate controls. Anti-emetic activity may also be demonstrated using other emetogens such as cisplatin and ipecacuanha.

Compounds of the invention have been shown to inhibit radiation-induced emesis at a dose of 0.3–3 mg/kg s.c. in the above test.

The compounds of the invention are potent and specific $NK_1$ antagonists. Furthermore, they exhibit good oral bioavailability and have an advantageous duration of action.

Compounds of the invention are useful as analgesics in particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful as antiinflammatory agents in particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders in particular allergic disorders of the skin such as urticaria, and allergic disorders of the airways such as rhinitis.

Compounds of the invention may also be useful in the treatment of CNS disorders in particular psychoses such as schizophrenia, mania, dementia or other cognitive disorders e.g. Alzheimer's disease; anxiety; AIDS related dementia; diabetic neuropathy; multiple sclerosis; depression; Parkinson's disease; and dependency on drugs or substances of abuse; and also the compounds of the invention may act as myorelaxants and antispasmodics.

Compounds of the invention are also useful in the treatment of emesis, i.e. nausea, retching and vomiting. Emesis includes acute emesis, delayed emesis and anticipatory emesis. The compounds of the invention, are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5- fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Compounds of the invention are also useful in the treatment of gastrointestinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

The compounds of the invention are of particular use in the treatment of emesis, migraine and as analgesics.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins, including substance P and other neurokinins.

In an alternative or further aspect there is provided a method for the treatment of a mammal, including man, in particular in the treatment of conditions mediated by tachykinins, including substance P and other neurokinins, comprising administration of an, effective amount of a compound of formula (I) or a pharmaceutically acceptable salt thereof.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or coloring agents. Drops may be formulated with an aqueous or non aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unit dose device or alternatively as a powder mix with a suitable carrier for administration using a suitable delivery device.

A proposed dose of the compounds of the invention is 0.05 mg/kg to about 400 mg/kg bodyweight per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

The compounds of formula (I) may, if desired, be administered with one or more therapeutic agents and formulated for administration by any convenient route in a conventional manner. Appropriate doses will be readily appreciated by those skilled in the art. For example, the compounds of formula (I) may be administered in combination with a systematic anti-inflammatory corticosteroid such as methyl prednisolone or dexamethasone, or a $5HT_3$ antagonist such as ondansetron, granisetron or metoclopramide. Antagonists of tachykinins, including substance P and other neurokinins, for example, the compounds of formula (I), may also be administered in combination with sympathomimetics such as ephedrine, pseudoephedrine and oxymetazoline.

Compounds of formula (I), and salts and solvates thereof, may be prepared by the general methods outlined hereinafter. In the following description, the groups R, $R^1$ and $R^2$ and x are as previously defined for compounds of formula (I) unless otherwise stated.

According to general process (A), a compound of formula (I) may be prepared by reacting a compound of formula (II):

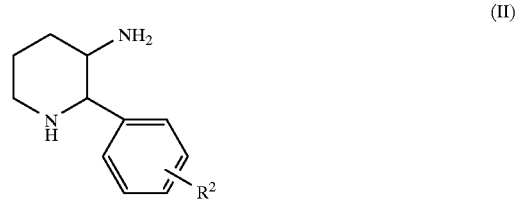

(II)

with a compound of formula (III)

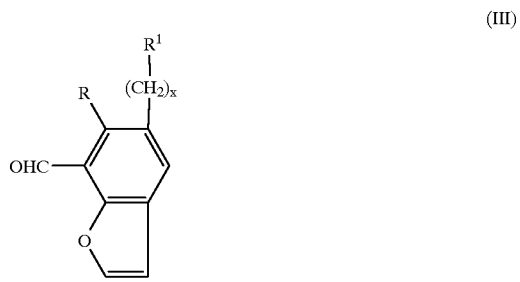

(III)

to form the intermediate imine, which may be isolated if required, followed by reduction of the imine using a suitable metal reducing agent such as a metal hydride, for example a borane hydride, alane hydride or a metal hydride complex like lithium aluminum hydride or sodium borohydride, or an organo-metallic complex such as borane-methyl sulphide, 9-borabicyclononane (9-BBN), triethylsilane, sodium triacetoxyborohydride, sodium cyanoborohydride and the like. Alternatively, catalytic hydrogenation may be used, for example using a platinium catalyst in a suitable solvent e.g. ethanol.

The condensation reaction conveniently takes place in a suitable solvent such as an alcohol (e.g. methanol), an aromatic hydrocarbon (e.g. benzene, toluene or xylene) or a chlorinated hydrocarbon (e.g. dichloromethane or dichloroethane) at a temperature ranging from ambient to the reflux temperature of the reaction mixture. The reaction preferably takes place in the presence of a catalytic amount of a suitable acidic condensing agent such as p-toluenesulphonic acid or acetic acid and/or a dehydrating agent such as molecular sieves, or the reaction may take place under Dean-Stark conditions.

The reduction step conveniently takes place in a suitable solvent such as acetonitrile, dimethylformamide, benzene, chlorinated hydrocarbons such as dichloromethane or dichloroethane, ethers such as diethyl ether, tetrahydrofuran, dioxane and 1,2-dimethoxyethane and alcohols such as ethanol at a temperature ranging from 0° C. to the reflux temperature of the reaction mixture.

Process (A) may also take place in one step without isolation of the intermediate imine if the condensation reaction takes place in the presence of sodium cyanoborohydride or sodium triacetoxyborohydride. Further reduction is therefore unnecessary in this case.

Compounds of formula (III) may be prepared by treating compounds of formula (IV)

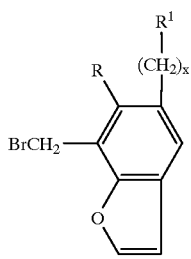

(IV)

with, for example, sodium bicarbonate or sodium carbonate in dimethylsulphoxide at elevated temperature according to conventional procedures. Alternatively the reaction may be carried out by treating a compound of formula (IV) with a base, such as sodium hydroxide, followed by oxidation, for example using manganese dioxide.

Compounds of formula (IV) may be prepared by bromination of the compounds of formula (V)

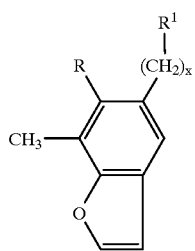

(V)

using, for example, N-bromosuccinimide and benzoyl peroxide according to conventional procedures.

Compounds of formula (V) may be prepared by cyclisation of compounds of formula (VI)

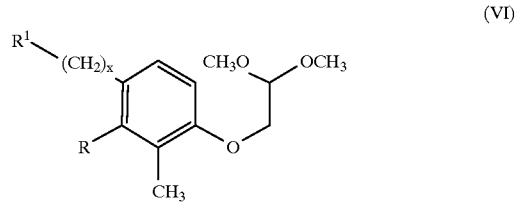

(VI)

using, for example, polyphosphoric acid according to conventional procedures.

Alternatively, compounds of formula (V) where R is hydrogen, $R^1$ represents an N-linked tetrazole ring and x is zero may be prepared by reacting 5-amino-7-methylbenzofuran with triethylorthoformate and sodium azide.

Compounds of formula (VI) may be prepared by reacting the compounds of formula (VII)

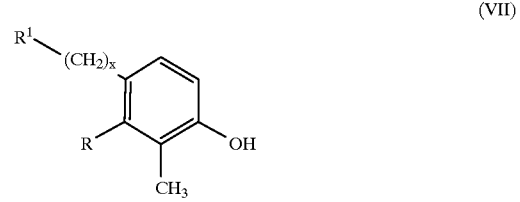

(VII)

with bromoacetaldehyde dimethylacetal in the presence of base according to conventional procedures.

Alternatively, compounds of formula (III) where R is hydrogen, $R^1$ is an N-linked tetrazole ring substituted by a trifluoromethyl group and x is zero may be prepared by reacting 5-azido-7-[1,3]dioxan-5-yl-benzofuran with trifluoromethyl substituted acetonitrile at elevated temperature and pressure, followed by deprotection.

5-azido-7-[1,3]dioxan-5-yl-benzofuran may be prepared according to the method described by Huber, M. L. and Pinhey, J. T., in *J. Chem. Soc. Perkin Trans.* 1, 1990, 721 from the acetic acid bis(acetoxy)-(7-[1,3]dioxan-2-yl-benzofuran-5-yl)-plumbanyl ester which may in turn be prepared from the corresponding tributylstannyl compound according to the method described by Kozyord, R. P., Morgan J. and Pinhey, J. T. in *Aust. J. Chem*, 1985, 38, 1147.

According to a further general process (B), a compound of formula (I) may be prepared by reacting a compound of formula (VIII)

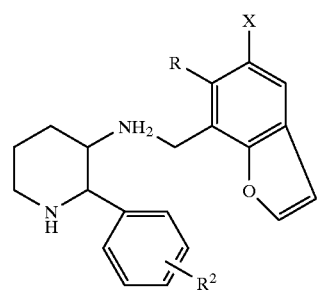

(VIII)

(where X is a suitable leaving group such as a halogen, i.e. bromine or iodine, atom or $OSO_2CF_3$ group) or a protected derivative thereof, with a compound of formula (IX)

 (IX)

(where Y represents B(OH)$_2$, or Sn(alkyl)$_3$ such as Sn(Me)$_3$ or Sn(Bu)$_3$ and R$^1$ and x are as defined above) followed by deprotection where necessary.

When Y is B(OH)$_2$, process (B) takes place in the presence of a palladium (O) catalyst such as tetrakis(triphenylphospbine) palladium (O). The reaction conveniently takes place in a suitable solvent such as an ether (e.g. dimethoxyethane) at an elevated temperature.

When Y is Sn(alkyl)$_3$, process (B) takes place in the presence of a palladium (II) catalyst such as bis(triphenylphosphine)palladium (II) chloride. The reaction conveniently takes place in a suitable solvent such as an aromatic hydrocarbon (e.g. toluene) at an elevated temperature.

Compounds of formula (VIII) may be prepared by reacting the compound of formula (II) with a compound of formula (X)

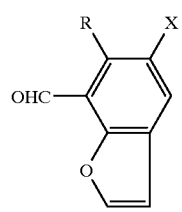 (X)

(where X is as defined above) under the conditions as described above for process (A). Compounds of formula (X) may be prepared by similar methods to those described for the preparation of compounds of formula (III).

In addition, compounds of formula (III) may be prepared under similar conditions as described for process (B). For example, compounds of formula (XI)

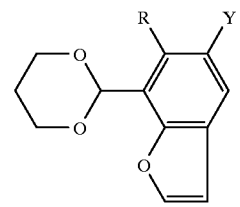 (XI)

where Y is as defined hereinbefore, for example Sn(alkyl)$_3$, may be reacted with compounds of formula (XII)

 (XII)

where X is as defined hereinbefore under appropriate conditions as described for the reaction of compounds of formula (VIII) and (IX) followed by deprotection.

It should be appreciated that in the above transformations it may be necessary or desirable to protect any sensitive groups in the molecule of the compound in question to avoid undesirable side reactions. For example it may be necessary to protect the nitrogen atoms, for example with an acyl (e.g. t-butyloxycarbonyl or benzyloxycarbonyl) group.

Protection and deprotection may be effected using conventional techniques such as those described in 'Protective Groups in Organic Synthesis 2nd Ed.' by T. W. Greene and P G M Wuts (John Wiley and Sons, 1991) and as described in the examples hereinafter.

Compounds of formulae (III), (IV), (V), (VI), (VIII) and (X) are novel and form a further feature of the invention. Compounds of formulae (II), (VII), (IX), (XI) and (XII) are either known, or may be prepared according to conventional procedures known for the preparation of analogous compounds.

Where it is desired to isolate a compound formula (I) as a salt, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether or tetrahydrofuran).

Pharmaceutically acceptable salts may also be prepared from other salts, including other pharmaceutically acceptable salts, of the compound of formula (I) using conventional methods.

The compounds of formula (I) may readily be isolated in association with solvent molecules by crystallisation from or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods.

Thus, in one example an appropriate optically active acid may be used to form salts with the enantiomeric mixture of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

A particularly suitable route for the preparation of optically active intermediates of formula (II) from the enantiomeric mixture thereof is by fractional crystallisation using (2R, 3R)-bis-(4-methyl-benzoyloxy)-succinic acid. Thus, the cis (S,S) form of intermediate (II) may be obtained from an enantiomeric mixture thereof (e.g. the racemic mixture) by fractional crystallisation with (2R, 3R)-bis-(4-methyl-benzoyloxy)-succinic acid in a suitable solvent, such as an aqueous alcohol, e.g. aqueous ethanol, isolating the resulting salt and converting it into the corresponding optically active free base by conventional procedures for example using aqueous ammonia.

Specific diastereoisomers of a compound of general formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which can then be separated by conventional means e.g. by chromatography or by fractional crystallisation. Alternatively, the diastereosiomers may be separable without the need for further derivatization.

Standard resolving methods are described for example in 'Stereochemistry of Carbon Compounds' by E. L. Eliel (McGraw Hill, 1962) and 'Tables of Resolving Agents' by S. H. Wilen.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples which are not intended as a limitation of the invention. All temperatures are in ° C. Flash column chromatography (FCC) was carried out on silica (Merck 9385). Unless otherwise indicated "drying" refers to drying over sodium sulfate. The following abbreviations are used: ether-diethyl ether.

INTERMEDIATE 1

4-Bromo-1-[(2,2-dimethoxyethyl)oxy]-2-methylbenzene

A mixture of 4-bromo-2-methylphenol (5 g), bromoacetaldehyde dimethyl acetal (3.8 ml) and potassium hydroxide (3.0 g) in dimethylsulphoxide (15 ml) was heated to reflux for 2½ h. Water (50 ml) was added to the cooled mixture which was then extracted with ether (4×50 ml). The extracts were washed with 5N sodium hydroxide (50 ml) and brine (50 ml), dried (MgSO4), then evaporated in vacuo to give the title compound as a brown oil (6 g).

T.l.c. ether-hexane 1:10, Rf 0.22.

INTERMEDIATE 2

5-Bromo-7-methyl-benzofuran

A solution of 4-bromo-1-[(2,2-dimethoxyethyl)oxy]-2-methylbenzene (5 g) in toluene (5 ml) was added to a mixture of polyphosphoric acid (2 g) and toluene (20 ml) at reflux, and the resulting dark mixture heated at reflux for 4 h. The solvent was decanted from the cooled mixture which was washed with further toluene (2×20 ml). The residue was dissolved in 2N sodium carbonate (20 ml) and was extracted with dichloromethane (3×20 ml). The combined, dried (MgSO4) organics were evaporated in vacuo and the dark residue purified by Kugelrohr distillation (8 mbar, 150°) to give a mixture of starting material and product as a colorless oil (4.1 g). The mixture was purified by FCC eluting with dichloromethane-hexane (1:3) to give the title compound as an oil (1.33 g).

T.l.c. dichloromethane-hexane 1:3, Rf 0.25

INTERMEDIATE 3

5-Bromo-7-bromomethyl-benzofuran

A mixture of 5-bromo-7-methyl-benzofuran (1.01 g), N-bromosuccinimide (1.04 g) and benzoyl peroxide (58 mg) in carbon tetrachloride (10 ml) was heated at reflux for 4 h under a 250 W tungsten lamp. A further portion of benzoyl peroxide (58 mg) was added and heating and irradiation continued for a total of 9 h. The reaction mixture was allowed to cool, diluted with chloroform (30 ml) and washed with 2N sodium hydroxide (40 ml) and then brine (40 ml). The organic phase was dried, filtered and the filtrate evaporated in vacuo to give the title compound as a brown oil (1.57 g).

T.l.c. hexane, Rf 0.27

INTERMEDIATE 4

(5-Bromo-benzofuran-7-yl)-methanol

5-Bromo-7-bromomethyl-benzofuran (1.50 g) in 1,4-dioxan (10 ml) and 2N sodium hydroxide (10 ml) was heated at reflux for 4 h, then left to stand at room temperature for 18 h. The reaction mixture was extracted with chloroform (2×30 ml), the organic phases were dried, filtered and the filtrate evaporated in vacuo to give an orange oil (1.10 g). Purification by FCC eluting with hexane-ethyl acetate (2:1) gave the title compound as a yellow solid (359 mg).

T.l.c. hexane-ethyl acetate 2:1, Rf 0.20

INTERMEDIATE 5

5-Bromo-benzofuran-7-carbaldehyde

A solution of (5-bromo-benzofuran-7-yl)-methanol (327 mg) in 1,4-dioxan (20 ml ) was treated with manganese dioxide (371 mg) and heated at reflux for 2 h. The reaction mixture was filtered, the cake was washed with chloroform (30 ml) and the combined filtrates were evaporated in vacuo to give the title compound as an orange solid (309 mg).

T.l.c. hexane-ethyl acetate 2:1, Rf 0.34

INTERMEDIATE 6 cis-(5-Bromo-benzofuran-7-ylmethyl)-(2-phenyl-piperidin-3-yl)-amine, dihydrochloride A solution of cis-3-amino-2-phenyl-piperidine (242 mg), 5-bromo-benzofuran-7-carbaldehyde (286 mg), and acetic acid (89 mg) in dry dichloromethane (20 ml) was treated with sodium triacetoxyborohydride (395 mg) and left to stir at room temperature for 18 h. 8% Sodium bicarbonate (15 ml) was added and the reaction mixture was left to stir for ½ h, the phases were separated, and the aqueous phase was extracted with chloroform (20 ml). The combined organic phases were dried, filtered and the filtrate evaporated in vacuo to give a yellow oil. Purification by FCC eluting with dichloromethane-ethanol-ammonia (200:8:1→100:8:1) gave a clear oil (392 mg). The oil was redissolved in ethanol (30 ml), treated with ethereal hydrogen chloride and solvent removed in vacuo to give a white powder. Recrystallisation from isopropanol-ethanol gave the title compound as a fluffy white powder (266 mg), m.p. 264–265°.

Similarly prepared:

INTERMEDIATE 7

1-[7-(2S-Phenyl-piperidin-3S-ylamino-methyl)-benzofuran-5-yl]-bicarbamic acid di-tert-butyl ester as a yellow gum (567 mg)

T.l.c. SiO2 (dichloromethane:ethanol:ammonia 100:8:1) Rf 0.32.

From 3S-amino-2S-phenyl-piperidine (244 mg) and 1-(7-formyl-benzofuran-5-yl)-bicarbamic acid di-tert-butyl ester (473 mg).

INTERMEDIATE 8 cis-3-[(5-Bromo-benzofuran-7-ylmethyl)tert-butoxycarbonyl-amino]-2-phenyl-piperidine-1-carboxylic acid tert-butyl ester A solution of cis-(5-bromo-benzofuran-7-ylmethyl)-(2-phenyl-piperidin-3-yl)-amine, dihydrochloride (1.69 g) in dichloromethane (50 ml) was treated successively with ethyldiisopropylamine (270 ml) and di-tert-butyldicarbonate (1.84 g) and left to stir at room temperature for 15 h. The reaction mixture was washed with 2N sodium carbonate (80 ml), dried, filtered and the filtrate evaporated in vacuo to give a yellow oil. Purification by FCC eluting with hexane-ethyl acetate (4:1) gave the title compound as a yellow gum (2.70 g).

T.l.c hexane-ethyl acetate 1:1, Rf 0.47

INTERMEDIATE 9

1-Methyl-5-tributylstannanyl-1H-[1,2,3]-triazole

A solution of 1-methyl-1H-[1,2,3]-triazole (0.25 g) in dry tetrahydrofuran (1.5 ml) was added, over 4 min, under nitrogen to a stirred, cooled (dry ice-acetone) mixture of n-butyl lithium (1.6M in hexane; 2 ml) and tetrahydrofuran (5 ml). After 40 min, tributylchlorostannane (0.87 ml) was added over 2 min. After a further 10 min, the cooling bath was removed and the mixture allowed to warm to room temperature. The mixture was diluted with brine (30 ml) and extracted with ethyl acetate (40 ml). The extract was washed with brine (20 ml), dried (MgSO4) and the solvent removed in vacuo to leave a colourless oil (1.5 g). Purification by FCC, eluting with ether-hexane then ether gave the title compound as a colorless oil (0.725 g).

T.l.c. (SiO2) Et2O, Rf 0.48

INTERMEDIATE 10

5-(1-Methyl-1H-[1,2,3]triazol-5-yl)-benzofuran-7-carbaldehyde

A mixture of 5-bromo-benzofuran-7-carbaldehyde (0.315 g), 1-methyl-5-tributylstannanyl-1H-[1,2,3]-triazole (0.525 g) and bis(triphenylphosphine)palladium (II) chloride (0.05 g) in toluene (7 ml) was stirred and refluxed under nitrogen for 5 h. The cooled mixture was diluted with 8% sodium bicarbonate (30 ml) and extracted with ethyl acetate (3×25 ml). The combined extracts were dried (MgSO4) and the solvent removed in vacuo to give a yellow solid (0.8 g). Purification by FCC, eluting with ethyl acetate-hexane, then ethyl acetate gave a cream solid, which was crystallised from ethyl acetate to give the title compound as pale green crystals (0.18 g), m.p. 180–2°.

INTERMEDIATE 11

5-Acetyl-benzofuran-7-carbaldehyde

A mixture of 5-bromo-benzofuran-7-carbaldehyde (2.00 g), 1-ethoxy-1-tributylstannanylethene (3.53 g)and bis(triphenylphosphine)palladium (II) chloride (63 mg) in dry toluene (4 ml) was heated at reflux under nitrogen for 18 h. A further portion of palladium catalyst (63 mg) was added and heating at reflux continued for a further 6 h. The reaction was allowed to cool, diluted with ether (40 ml) and filtered through a plug of Hyflo. The filtrate was washed successively with hydrochloric acid (50 ml; 2M) and brine (50 ml), then dried, and concentrated in vacuo to give an orange oil. Purification by FCC eluted with hexane to hexane:ethyl acetate (4:1) gave the title compound as a yellow powder (1.21 g), m.p. 91–93°.

INTERMEDIATE 12

1-(7-[1,3]dioxan-2-yl-benzofuran-5-yl)-4-trimethylsilanyl-1H-[1,2,3]triazole A stirred solution of 5-azido-7-[1,3]dioxan-5-yl-benzofuran and 1-trimethylsilyl ethyne (2 ml) were heated at 90° in a sealed vessel for 24 h. The solution was cooled and evaporated. The residual oil was purified by FCC eluted with hexane-ether 3:2. to give the title compound as a near colorless oil (187 mg).

T.l.c. (SiO$_2$) Hexane-ether 3:2, Rf 0.15,

INTERMEDIATE 13

5-[1,2,3]Triazol-1-yl-benzofuran-7-carbaldehyde

A solution of 1-(7-[1,3]dioxan-2-yl-benzofuran-5-yl)-4-trimethylsilanyl-1H-[1,2,3]triazole (180 mg) in potassium hydroxide (0.1 g), water (10 ml) and methanol (10 ml) was stirred for 18 h at room temperature. The solvent was removed, diluted with water (10 ml) and extracted with dichloromethane (3×15 ml). The organic extracts were washed with water (10 ml), dried, and evaporated. The residual oil was dissolved in hydrochloric acid (2M; 10 ml) and tetrahydrofuran (10 ml) and stirred at 70° for 30 min. The solution was cooled, basified with 1M sodium carbonate solution and extracted with dichloromethane (3×20 ml). The combined extracts were dried, and evaporated to give the title compound as a pale cream coloured solid (74 mg).

T.l.c. (SiO$_2$) Ether-hexane 1:1, Rf 0.2.

INTERMEDIATE 14

1-(7-[1,3]-Dioxan-2-ylbenzofuran-5-yl)-bicarbamic acid di-tert-butyl ester

A solution of 5-bromo-7-[1,3]-dioxan-2-ylbenzofuran (2.00 g in dry ether (80 ml) was cooled to −100° and treated dropwise with a solution tert-butyllithium (92 ml; 1.7M in pentane) over 10 min to maintain the temperature <−100°. The orange slurry was left to stir at −100° to −95° for 25 min, solid di-tert-butyl azodicarboxylate (1.72 g,) was added, the slurry was left to stir at −100° to −95° for 0.5 h, and then warmed to room temperature over 2 h. Saturated ammonium chloride solution (40 ml) was added, the phases were separated, the organic phase was washed with brine (75 ml), dried, filtered and the filtrate evaporated in vacuo to give an orange gum (3.52 g). Purification FCC eluting with hexane:ethyl acetate (3:1) gave the title compound as a yellow foam (1.48 g).

T.l.c. SiO2 (hexane:ethyl acetate 3:1) Rf 0.10.

INTERMEDIATE 15

1-(7-Formyl-benzofuran-5-yl)-bicarbamic acid di-tert-butyl ester

A solution of 1-(7-[1,3]-dioxan-2-yl-benzofuran-5-yl)-bicarbamic acid di-tert-butyl ester (51 mg) in acetone (5 ml)

and water (1 ml) was treated with pyridinium 4-methylphenylsulfonate (5 mg) and heated at reflux for 16 h. The reaction mixture was allowed to cool, solvent removed in vacuo, the residue was diluted with water (10 ml) and extracted with chloroform (2×10 ml). The combined organic phases were dried, filtered and the filtrate evaporated in vacuo to give the title compound as a clear oil (41 mg).

T.l.c. SiO2 (hexane:ethyl acetate, 2:1) Rf 0.34.

INTERMEDIATE 16

1-(7-Hydroxymethyl-benzofuran-5-yl)-ethanone

A solution of 5-acetyl-benzofuran-7-carbaldehyde (471 mg) in dry toluene (40 ml) was treated with sodium triacetoxyborohydride (1.12 ml) and heated at reflux for 5.5 h. The reaction mixture was poured into 8% sodium bicarbonate (40 ml) and the phases were separated. The aqueous phase was extracted with ethyl acetate (40 ml), the combined organic phases were dried, filtered, and the filtrate evaporated in vacuo to give a yellow gum. Purification by FCC eluted with hexane:ethyl acetate (2:1→1:1) gave the title compound as a pale yellow oil (275 mg) which slowly solidified.

T.l.c. SiO2 (hexane ethyl acetate, 1:1) Rf 0.26.

INTERMEDIATE 17

[5-(5-Methyl-tetrazol-1-yl)-benzofuran-7-yl]-methanol

A solution of 1-(7-hydroxymethyl-benzofuran-5-yl)-ethanone (250 mg,) and sodium azide (0.68 g) in acetonitrile (40 ml) was treated with titanium tetrachloride (0.29 ml) and heated at reflux for 1.5 h. The reaction mixture was allowed to cool, treated with 2N hydrochloric acid (40 ml) and extracted with ethyl acetate (2×40 ml). The organic phases were dried, combined, filtered and the filtrate evaporated in vacuo to give a yellow oil. Purification by FCC eluted with hexane:ethyl acetate (1:3) gave the title compound as a clear gum (131 mg).

T.l.c. SiO2 (hexane:ethyl acetate 1:3) Rf 0.14

INTERMEDIATE 18

5-(5-Methyl-tetrazol-1-yl)-benzofuran-7-carbaldehyde

[5-(5-Methyl-tetrazol-1-yl)-benzofuran-7-yl]-methanol (124 mg,) and manganese (IV) oxide (140 mg) in 1,4-dioxan (5 ml) was heated at reflux for 18 h. A further portion of manganese (IV) oxide (210 mg) was added and heating continued for 2 h. The reaction mixture was filtered through a plug of Hyflo, the pad was washed with chloroform (20 ml) and the filtrate was evaporated in vacuo to give the title compound as a white powder (77 mg).

T.l.c. SiO2 (hexane:ethyl acetate 1:3) Rf 0.23.

INTERMEDIATE 19

7-[1,3]Dioxan-2-yl-5-trimethylsilyl-ethynyl-benzofuran

A solution of 5-bromo-7-[1,3]-dioxan-2-ylbenzofuran (500 mg) in triethylamine in a sealed vessel was degassed by bubbling nitrogen through the solution for 15 min. The solution was treated with trimethylsilanylethyne (346 mg), bis(triphenylphosphine)palladium (II) chloride (31 mg) and copper iodide (12 mg). The vessel was flushed with nitrogen, sealed and heated at 100° C. for 4 h. The cooled vessel was opened and the reaction mixture treated with bis (triphenylphosphine)palladium (II) chloride (31 mg) and copper iodide (12 mg). The vessel was then flushed with nitrogen, resealed and heated at 100° for a further 16 h. The cooled vessel was opened and the reaction mixture poured onto ether (25 ml), filtered through Hyflo and evaporated in vacuo to give a black oil. Purification by FCC eluting with hexane:ethyl acetate (4:1) gave the title compound as a yellow/brown oily solid (330 mg).

T.l.c. SiO2 Hexane:ethyl acetate (2:1), Rf=0.51

INTERMEDIATE 20

7-[1,3]Dioxan-2-yl-5-ethynyl-benzofuran

A mixture of 7-[1,3]dioxan-2-yl-5-trimethylsilylethynyl-benzofuran (330 mg), and potassium carbonate (40 mg) in anhydrous methanol (10 ml) was stirred at room temperature for 1 h. The solvent was removed in vacuo, the residue treated with water (50 ml), and extracted with ether (3×75 ml). The combined organic extracts were washed with sodium hydroxide (50 ml; 2M), dried, and evaporated in vacuo to give the title compound as a brown oil (247 mg).

TlC SiO2 Hexane:ethyl acetate 2:1, Rf=0.43

INTERMEDIATE 21

4-(7-[1,3]Dioxan-2-yl-benzofuran-5-yl)-2H-[1,2,3] triazole

A mixture of 7-[1,3]dioxan-2-yl-5-ethynyl-benzofuran (247 mg) and tributylstannanyl azide (717 mg) was heated at 140° in a sealed vessel for 24 h. Purification by FCC eluting with hexane:ethyl acetate 2:1 gave the title compound as a yellow oil (80 mg).

T.l.c. SiO2 Hexane:ethyl acetate (2:1), Rf=0.12

INTERMEDIATE 22

5-(2H-[1,2,3]triazol-4-yl)-benzofuran-7-carbaldehyde

A solution of 4-(7-[1,3]dioxan-2-yl-benzofuran-5-yl)-2H-[1,2,3]triazole (80 mg) in hydrochloric acid (2M; 10 ml) and tetrahydrofuran was heated at reflux for 0.5 h. The cooled reaction mixture was treated with sodium hydroxide (25 ml; 2M) and extracted with ethyl acetate (3×50 ml). The combined organic extracts were dried, and evaporated in vacuo to give the title compound as a yellow/orange solid (60 mg).

T.l.c. SiO2 Hexane:ethyl acetate (2:1), Rf=0.14

Similarly prepared:

INTERMEDIATE 23

5-(2Methyl-2H-[1,2,4]triazol-3-yl)-benzofuran-7-carbaldehyde as a yellow oil (135 mg)

T.l.c. (SiO2) Hexane:ethyl acetate 1:3, Rf 0.3

From 5-(7-[1,3]-Dioxan-2-yl-benzofuran-5-yl)-1-methyl-1H-[1,2,4]triazole (171 mg).

INTERMEDIATE 24

5-(1H-Pyrazol-4-yl)-benzofuran-7-carbaldehyde (189 mg)

T.l.c. (SiO$_2$) Hexane-ethyl acetate 2:1, Rf 0.3.

From 1-Benzenesulfonyl-4-(7-[1,3]dioxan-2-yl-benzofuran-5-yl)-1H-pyrazole (300 mg).

INTERMEDIATE 25

5-(3,5-Dimethyl-1H-Pyrazol-4-yl)-benzofuran-7-carbaldehyde (40 mg)

T.l.c. (SiO$_2$) Dichloromethane-ethanol-ammonia 200:8:1, Rf 0.26.

From 1-Benzenesulfonyl-4-(7-[1,3]dioxan-2-yl-benzofuran-5-yl)-3,5-dimethyl-1H-pyrazole (80 mg).

INTERMEDIATE 26

5-(3-Methyl-3H-imidazol-4-yl)-benzofuran-7-carbaldehyde (74 mg)

T.l.c. (SiO$_2$) Dichloromethane-ethanol-ammonia 200:8:1, Rf 0.5.

From 5-(7-[1,3]dioxan-2-yl-benzofuran-5-yl)-1-methyl-1H-imidazole (118 mg).

INTERMEDIATE 27

5-(7-[1,3]Dioxan-2-yl-benzofuran-5-yl)-1-methyl-1H[1,2,4]triazole

A mixture of tributyl-(7-[1,3]dioxan-2-ylbenzofuran-5-yl)stannane (839 mg), 5-bromo-1-methyl-1H-[1,2,4]triazole (396 mg), bis(triphenylphosphine)palladium (II) chloride (59 mg) in dry toluene (10 ml) was heated at reflux for 42 h. The cooled solution was then filtered through Hyflo and the filtrate washed with 10% potassium fluoride solution (30 ml). The organic layer was washed with brine (30 ml), dried, and evaporated in vacuo to give a yellow oil. The crude material was purified by FCC eluting with hexane:ethyl acetate (1:1→1:3) to give the title compound as a yellow oil (171 mg,).

T.l.c. (SiO2) Hexane:ethyl acetate 1:3, Rf 0.29

Similarly prepared:

INTERMEDIATE 28

5-(3,5-Dimethyl-isoxazol-4-yl)-benzofuran-7-carbaldehyde (153 mg)

T.l.c. (SiO$_2$) Hexane-ethyl acetate 2:1, Rf 0.47.

From tributyl-(7-[1,3]dioxan-2-yl-benzofuran-5-yl)-stannane (1.43 g) and 4-bromo-3,5-dimethylisoxazole (0.51 g).

INTERMEDIATE 29

5-(2-Methyl-2H-pyrazol-3-yl)-benzofuran-7-carbaldehyde (288 mg) as a yellow solid, m.p. 119–110° C.

From 1-Methyl-5-tributylstannanyl-1H-pyrazole (826 mg) and 5-bromo-benzofuran-7-carboxaldehyde (500 mg).

INTERMEDIATE 30

5-Thiazol-2-yl-benzofuran-7-carbaldehyde (200 mg) as a pale yellow solid, m.p. 100–103°

From 5-Bromo-benzofuran-7-carbaldehyde (400 mg) and 2-trimethylstannanylthiazole (1.22 g).

INTERMEDUATE 31

5-(3-Pyridyl)-benzofuran-7-carboxaldehyde (90 mg) as a cream solid, m.p. 100–101°.

From 5-Bromo-benzofuran-7-carboxaldehyde (300 mg) and 3-trimethylstannanyl-pyridine (420 mg).

INTERMEDIATE 32 cis-2-Phenyl-3-[(5-pyrimidin-5-yl-benzofuran-7-ylmethyl)tert-butoxycarbonyl-amino]-piperidine-1-carboxylic acid tert-butyl ester (190 mg)

T.l.c. hexane-ethyl acetate 1:3, Rf 0.13 plus cis-2-phenyl-3-[(5-pyrimidin-5-yl-benzofuran-7-ylmethyl)amino]-piperidine-1-carboxylic acid tert-butyl ester (90 mg).

T.l.c. hexane-ethyl acetate 1:3, Rf 0.12

From cis-3-[(5-bromobenzofuran-7-ylmethyl)tert-butoxycarbonyl-amino]-2-phenyl-piperidine-1-carboxylic acid tert-butyl ester (600 mg) and 5-tributylstannanyl-pyrimidine (458 mg)

INTERMEDIATE 33 cis-2-Phenyl-3-[(5-pyridin-2-yl-benzofuran-7-ylmethyl)tert-butoxycarbonyl-amino]-piperidine-1-carboxylic acid tert-butyl ester (293 mg) as a yellow oil T.l.c. hexane-ethyl acetate 1:1, Rf 0.39.

From cis-3-[(5-bromobenzofuran-7-ylmethyl)tert-butoxycarbonyl-amino]-2-phenyl-piperidine-1-carboxylic acid tert-butyl ester (409 mg) and 2-tributylstannanyl-pyridine (339 mg).

INTERMEDIATE 34

5-(1-Methyl-1H-[1,2,3]triazol-4-yl)-benzofuran-7-carbaldehyde

A mixture of tributyl-(7-[1,3]dioxan-2-yl-benzofuran-5-yl)stannane (510 mg), 4-bromo-1-methyl-1H-[1,2,3]triazole (204 mg), tetrakis(triphenylphosphine) palladium (O) (59 mg) in dry toluene (7 ml) was heated at reflux for 18 h. The cooled solution was then filtered through Hyflo and the filtrate washed with 10% potassium fluoride solution (30 ml). The organic layer was washed with brine (30 ml), dried, and evaporated in vacuo to give a black oil. The oil was purified by FCC eluting with hexane:ethyl acetate (1:1) to give a colourless oil (80 mg). The oil was dissolved in tetrahydrofuran (5 ml), treated with hydrochloric acid (2M; 10 ml) and heated under reflux for 2 h. The cooled reaction mixture was then treated with sodium hydroxide (2M; 25 ml), extracted with ethyl acetate (3×50 ml), dried, and evaporated in vacuo to give the title compound as a yellow solid (69 mg).

T.l.c. (SiO2) Hexane:ethyl acetate 1:1, Rf 0.2

Similarly prepared:

INTERMEDIATE 35

5-(7-[1,3]Dioxan-2-yl-benzofuran-5-yl)-1-methyl-1H-imidazole (54 mg)

T.l.c. (SiO$_2$) Dichloromethane-ethanol-ammonia 200:8:1, Rf 0.15.

From tributyl-(7-[1,3]Dioxan-2-yl-benzofuran-5-yl)-stannane (0.40 g) and 5-bromo-1-methyl-1H-imidazole (0.13 g).

INTERMEDIATE 36

5-Bromo-7-[1,3]-dioxan-2-yl-benzofuran

A mixture of 5-bromo-benzofuran-7-carbaldehyde (400 mg), 4-methylphenylsulphonic acid (0.38 g) and 1,3-propanediol (10 ml) in toluene (15 ml) was heated at reflux for 19 h, with azeotropic removal of water by Dean-Stark Apparatus. The reaction mixture was cooled, diluted with water (80 ml) and extracted with toluene (30 ml). The organic phase was dried, filtered and the filtrate evaporated in vacuo to give a brown oil. Purification by FCC eluted with hexane:ethyl acetate (7:1→3:1) gave the title compound as a yellow solid (427 mg).

T.l.c. SiO2 Hexane:ethyl acetate 3:1 Rf 0.31

INTERMEDIATE 37

Tributyl-(7-[1,3]dioxan-2-yl-benzofuran-5-yl)-stannane

A solution of 5-bromo-7-[1,3]-dioxan-2-yl-benzofuran (329 mg), bis(tributylstannane) (1.8 ml) and tetrakis (triphenylphosphine)palladium (O) (72 mg) in dry toluene (15 ml) was heated at reflux for 2 h. A further portion of palladium catalyst (67 mg) was added, and heating at reflux continued for 16 h. The reaction mixture was cooled, diluted with 10% potassium fluoride solution (30 ml), left to stir for ½ h and filtered through a plug of Hyflo. The phases were separated, the organic phase was dried, filtered and the filtrate evaporated in vacuo to give a dark oil. Purification by FCC eluted with hexane:ethyl acetate (6:1) gave the title compound as a colourless oil (273 mg).

T.l.c. SiO2 Hexane:ethyl acetate 3:1, Rf 0.35

Similarly prepared:

INTERMEDIATE 38

1-Benzenesulfonyl-4-tributylstannanyl-1H-pyrazole (925 mg)

T.l.c. (SiO$_2$) Dichloromethane-hexane 1:1, Rf 0.1.

From 1-benzenesulfonyl-4-bromo-1H-pyrazole (3.013 g) and bis(tributylstannane) (11.24 g).

INTERMEDIATE 39

1-Benzenesulfonyl-3,5-dimethyl-4-tributylstannanyl-1H-Pyrazole (660 mg)

T.l.c. (SiO$_2$) Hexane-ethyl acetate 4:1, Rf 0.65.

From 1-benzenesulfonyl-4-bromo-3,5-dimethyl-1H-pyrazole (2.39 g) and bis(tributylstannane) (15.98 g).

INTERMEDIATE 40

5-(1-Methyl-1H-tetrazol-5-yl)-benzofuran-7-carbaldehyde

A mixture of tributyl-(7-[1,3]-dioxan-2-yl-benzofuran-5-yl)-stannane (660 mg), 5-bromo-1-methyl-1H-tetrazole (203 mg) and bis(triphenylphosphine)palladium (II) chloride (42 mg) in dry toluene (20 ml) was heated at reflux for 18 h. A further portion of 5-bromo-1-methyl-1H-tetrazole (206 mg) and bis(triphenylphosphine) palladium (II) chloride (56 mg) was added and heating continued for 24 h. The solvent was removed in vacuo and the residue purified by FCC eluted with hexane:ethyl acetate (1:1→1:3) to give the acetal intermediate (82 mg) as a white powder. The powder was redissolved in tetrahydrofuran (5 ml) and 2N hydrochloric acid (10 ml) and heated at reflux for 2 h. Solvent was removed in vacuo, the residue was basified with 2N sodium carbonate and extracted with chloroform (2×30 ml). The organic phases were dried, filtered, combined and evaporated in vacuo to give the title compound as a white powder (80 mg).

T.l.c. SiO2 Hexane:ethyl acetate 1:2, Rf 0.28

INTERMEDIATE 41

5-Phenyl-benzofuran-7-carbaldehyde

A mixture of 5-bromo-benzofuran-7-carbaldehyde (600 mg), phenylboronic acid (326 mg) and tetrakis (triphenylphosphine)palladium (O) (176 mg) in dimethoxyethane (20 ml) and 8% sodium bicarbonate (10 ml) was heated at reflux for 16 h. Solvent was removed in vacuo, the residue was partitioned between chloroform (40 ml) and water (40 ml). The organic phase was washed with brine (50 ml), dried, filtered and the filtrate evaporated in vacuo to give a yellow oil. Purification by FCC eluted with hexane-:ethyl acetate (1:0→10:1) gave the title compound as a pale yellow solid (214 mg).

T.l.c. SiO2 Hexane:ethyl acetate 3:1, Rf 0.48,

Similarly prepared:

INTERMEDIATE 42

6-Methoxy-5-pyridin-4-ylbenzofuran-7-carbaldehyde (240 mg)

T.l.c. (SiO$_2$) Ethyl acetate, Rf 0.23.

From 5bromo-6-methoxybenzofuran-7-carbaldehyde (350 mg) and pyridine-4-boronic acid (0.21g).

INTERMEDIATE 43

Acetic acid bis(acetoxy)-(7-[1,3]dioxan-2-yl-benzofuran-5-yl)-plumbanyl ester

A stirred solution of tributyl-(7-[1,3]dioxan-2-yl-benzofuran-5-yl)stannane (9.6 g), lead tetraacetate (9.8 g) and mercuric acetate (350 mg) in chloroform (200 ml) was heated at 45° for 20 h. The mixture was cooled and filtered through Hyflo. The filtrate was evaporated to dryness. The residual gum was triturated under hexane (200 ml) for 2 h to give the title compound as an off-white solid (9.4 g), m.p. 92–94°.

INTERMEDIATE 44

5-Azido-7-[1,3]dioxan-5-yl-benzofuran

Sodium azide (10.4 g) and acetic acid bis(acetoxy)-(7-[1, 3]dioxan-2-yl-benzofuran-5-yl)-plumbanyl ester in dimethylsulphoxide (120 ml) were stirred for 3 h at room temperature. The mixture was poured into water (1000 ml) and extracted with ethyl acetate (4×100 ml). The combined, dried, organics were evaporated to give the title compound as a pale brown solid (3.5 g). A portion was purified by FCC using hexane-ether (3:1) as eluent to give the title compound as an off-white solid, m.p. 102–104°.

INTERMEDIATE 45

7-([1,3]-Dioxan-2-yl)-5-(5-trifluoromethyl-tetrazol-1-yl)-benzofuran

5-Azido-7-[1,3]-dioxan-5yl-benzofuran (150 mg) was dissolved in trifluoroacetonitrile (3 ml) at 0° C. in a sealed 10 ml stainless steel vessel. The vessel was heated at 150° C. for 18 h. The vessel was re-cooled to 0° C. and the pressure released. The crude material was purified by FCC eluted with dichloromethane to give the title compound (15 mg) as an oil which solidified on standing.

T.l.c. (SiO2) Dichloromethane, Rf 0.17.

INTERMEDIATE 46

5-(5-Trifluoromethyl-tetrazol-1-yl)-benzofuran-7-carbaldehyde 7-([1,3]-Dioxan-2-yl)-5-(5-trifluoromethyl-tetrazol-1-yl)-benzofuran (160 mg) was dissolved in tetrahydrofuran (30 ml) and dilute hydrochloric acid (20 ml; 2M). The reaction mixture was heated to reflux and stirred for a total of 3 h, cooled and concentrated in vacuo. The residue was taken up in chloroform (40 ml), and the organic phase washed with 8% sodium bicarbonate solution (3×20 ml), dried and concentrated in vacuo. The crude material was purified by FCC eluted with dichloromethane-hexane (1:1) to dichloromethane-hexane (2:1) to give the title compound (100 mg) as an oil.

T.l.c. (SiO2) Toluene, Rf 0.09.

INTERMEDIATE 47

5-(4-methanesulfonyl-phenyl)-benzofuran-7-carbaldehyde

Tributyl-7-[1,3]dioxan-2-yl-benzofuran-5-yl)-stannane (508 mg), 4-methanesulfonylbromobenzene (267 mg) and bis(triphenylphosphine)palladium (II) chloride (36 mg) were dissolved in dry dimethylformamide (15 ml) and heated at 120° C. for 0.5 h. The reaction was cooled, diluted with water (20 ml) and extracted with ether (3×40 ml). The combined organic phases were dried, and concentrated in vacuo to give a yellow solid (800 mg). The crude solid was dissolved in dilute hydrochloric acid (20 ml; 2M) and tetrahydrofuran (10 ml) and heated at reflux for 16 h. The solvent was removed in vacuo and the residue was poured into 8% sodium bicarbonate, extracted with chloroform (2×40 ml), dried, and concentrated in vacuo. The crude material was purified by FCC eluted with hexane-ethyl acetate (1:2) to give the title compound (274 mg) as an off white solid.

T.l.c. (SiO2) Hexane-ethylacetate (1:2) Rf 0.23.

INTERMEDIATE 48

2-(4-Fluorophenyl)-3-nitropyridine

Tetrakis(triphenylphosphine)palladium(O) (1.65 g) was added to a solution of 2-chloro-3-nitropyridine (4.60 g) in dimethoxyethane (50 ml, degassed) under nitrogen and stirred for 10 mins. 4-Fluorophenylboronic acid (5.99 g) in ethanol (25 ml, degassed) followed by aqueous sodium carbonate (2 M, 50 ml) were added and the mixture was heated under reflux overnight. Additional tetrakis (triphenylphosphine)palladium(O) (1.3 g) and water (20 ml) were added. After another 36 h at reflux, the cooled mixture was filtered through Hyflo, washed with ethyl acetate and dimethoxyethane. The filtrate was evaporated in vacuo to remove most organic solvent. The resultant aqueous oily solution was diluted with saturated aqueous sodium bicarbonate (100 ml) and extracted with ethyl acetate (2×100 ml). Combined organic solutions were washed with brine, dried ($MgSO_4$) and evaporated to give a brown oil (9.51 g). FCC eluted with cyclohexane:ethyl acetate, (4:1) gave the title compound as a yellow solid (5.07 g). δ ($d^6$-DMSO) 7.35 (t, 2H, J=8.5 Hz), 7.62 (dd, 2H, J=8.5 and 5.5 Hz), 7.71 (dd, 1H, J=8.0 and 5.0 Hz), 8.48 (d, 1H, J=8.0 Hz), 8.94 (d, 1H, J=5.0 Hz).

Similarly prepared:

INTERMEDIATE 49 cis-3-[(5-Furan-3-yl-benzofuran-7-ylmethyl)tert-butoxycarbonyl-amino]-2-phenyl-piperidine-1-carboxylic acid tert-butyl ester (388 mg)

T.l.c. hexane-ether 1:1, Rf 0.34

From cis-3-[(5-bromobenzofuran-7-ylmethyl)tert-butoxycarbonyl-amino]-2-phenyl-piperidine-1-carboxylic acid tert-butyl ester (473 mg) and 3-furanboronic acid (102 mg).

INTERMEDIATE 50 cis-2-4-Fluorophenyl)-3-piperidinamine

A mixture of 2-(4-fluorophenyl)-3-nitropyridine (4.88 g) and platinum oxide (1.50 g) in ethanol (200 ml) and concentrated hydrochloric acid (15 ml) was stirred under an atmospheric pressure of hydrogen and at room temperature for 22 h. The mixture was diluted with water (100 ml), filtered through Hyflo and washed with water. The filtrate was evaporated under reduced pressure to give a white-yellow solid, washed twice with small amount of ethanol and dried in vacuo at 50° overnight to give the dihydrochloride salt (4.16 g). This dihydrochloride salt was partitioned between concentrated ammonia (100 ml) and chloroform (100 ml). The aqueous solution was extracted further with chloroform (2×100 ml). Combined organic solutions were dried ($MgSO_4$), filtered and evaporated to give the title compound as a colorless oil (3.08 g).

Mass spec. $MH^+$195.

INTERMEDIATE 51

2S-(4-Fluoro-phenyl)-piperidin-3S-ylamine-2R,3R-bis-(4-methyl-benzoyloxy)-succinate cis-2-(4-Fluorophenyl)-3-piperidinamine (1.0 g) was dissolved in ethanol (70 ml) and water (10 ml). The solution was heated to 60° and (2R, 3R)-bis-(4-methyl-benzyloxy)-succinic acid (2.0 g) was added. The mixture was cooled to room temperature and the precipitate was collected by filtration, washed with a little ethanol and dried in vacuo at 40° (1.25 g). A sample of this salt (1 g) was recrystallised from a mixture of ethanol (51 ml) and water (9.5 ml) to give the title compound as white crystalline solid (803.5 mg). δ (CD$_3$OD) includes 1.5–2.2 (m, 5H), 2.4 (s, 6H), 2.85–3.05 (m, 1H), 3.5–3.6 (m, 1H), 4.27 (d, 1H, J=2H), 7.0 (t, 2H, J=8.7 Hz), 7.3 (d, 4H, J=8.5 Hz), 7.45 (dd, 2H, J=8.7 and 5 Hz). Chiral HPLC on a CHIRALCEL-OD-H column eluting with hexane containing 2% isopropyl alcohol showed only one enantiomer (t$_R$=35.83 mins).

INTERMEDIATE 52

7-Methyl-5-nitro-2,3-dihydrobenzofuran

Acetyl chloride (6.2 ml) in acetonitrile (20 ml) was added dropwise over 20 min. to a solution of silver nitrate (14.6 g) and 7-methyl-2,3-dihydrobenzofuran (9.6 g) in acetonitrile (100 ml), maintaining a temperature of 5–10°. The reaction was maintained at 5–10° for 1 h, warmed to room temperature then stirred for a further hour. Water (50 ml) was added and the mixture concentrated in vacuo. The resulting precipitate was filtered and dried in vacuo to afford the title compound as a brown solid (9.5 g), m.p. 80–81°.

T.l.c. (SiO$_2$) Ether-hexane 1:1, Rf 0.5.

INTERMEDIATE 53

5-Amino-7-methyl-2,3-dihydrobenzofuran

A solution of 7-methyl-5-nitro-2,3-dihydrobenzofuran (2 g) in ethanol (25 ml) was hydrogenated over palladium on carbon catalyst overnight. The catalyst was filtered off and the solvent removed in vacuo. The residue was partitioned between ether (30 ml) and hydrochloric acid (2M; 30 ml), the acid layer removed and the organic extracted with further acid. The combined acidic extracts were basified with 5M sodium hydroxide and extracted with ether (4×25 ml). The combined, dried (MgSO$_4$), extracts were evaporated in vacuo to give the title compound as a brown solid (0.7 g).

T.l.c. (SiO$_2$) Ether-hexane 1:1, Rf 0.12

INTERMEDIATE 54

2,2,2-Trifluoro-N-(7-methyl-2,3-dihydrobenzofuran-5-yl)-acetamide

Trifluoroacetic anhydride (7.3 ml) was added dropwise to an ice cooled solution of 5-amino-7-methyl-2,3-dihydrobenzofuran (7.3 g) and triethylamine (7.3 ml) in dichloromethane (100 ml) and the resulting mixture stirred at room temperature for 45 mins. The solution was washed with 8% sodium bicarbonate solution (50 ml) then hydrochloric acid (2M; 50 ml), dried (MgSO$_4$), and evaporated in vacuo to afford the title compound as a dark solid (11.9 g).

T.l.c. (SiO$_2$) Ether-hexane 1:1, Rf 0.45.

INTERMEDIATE 55

2,2,2-Trifluoro-N-(7-methyl-benzofuran-5-yl)-acetamide 2,3-Dichloro-5,6-dicyano-1,4-benzoquinone (1.3 g) was added to a solution of 2,2,2-trifluoro-N-(7-methyl-2,3-dihydro-benzofuran-5-yl)-acetamide (600 mg) in carbon tetrachloride (30 ml) and the resulting mixture heated at reflux for 4.5 hours. The reaction mixture was filtered, the filtrate adsorbed on to silica and the residue purified by FCC eluting with ether-hexane (1:1) to give the title compound as a peach solid (590 mg), m.p. 96–97°.

T.l.c. (SiO$_2$) Ether-hexane 1:1, Rf 0.57.

INTERMEDIATE 56

5-Amino-7-methyl-benzofuran

A mixture of 2,2,2trifluoro-N-(7-methyl-benzofuran-5-yl)-acetamide (580 mg) and potassium carbonate (1.64 g) in methanol (25 ml) and water (2.5 ml) was heated at reflux for 2.5 hours. The residue was extracted with dichloromethane (3×25 ml) and the combined, dried (MgSO$_4$) organic phase was evaporated in vacuo to give the title compound as a colourless oil (350 mg).

T.l.c. (SiO$_2$) Ether-hexane 1:1, Rf 0.17.

INTERMEDIATE 57

1-(7-Methyl-benzofuran-5-yl)-1H-tetrazole

A mixture of 5-amino-7-methyl-benzofuran (350 mg) and triethylorthoformate (0.42 ml) in glacial acetic acid (10 ml) was heated at 80° for 1 hour. Sodium azide (470 mg) was added and stirring continued at 80° C. for 4 hours. The mixture was partitioned between ethyl acetate (25 ml) and 8% sodium bicarbonate solution (40 ml), the aqueous was further extracted with ethyl acetate (2×25 ml). The combined organic extracts were washed with hydrochloric acid (2M:25 ml), dried (MgSO$_4$), and evaporated in vacuo. The residue was purified by FCC eluting (with ether-hexane (3:1) to give the title compound as a white solid (174 mg), m.p. 118°.

T.l.c. (SiO$_2$) Ether-hexane 1:1, Rf 0.17.

INTERMEDIATE 58

5-Tetrazol-1-yl-benzofuran-7-carbaldehyde

N-Bromosuccinimide (180 mg) was added to a hot solution of 1-(7-methyl-benzofuran-5-yl)-1H-tetrazole and azoisobutyronitrile (35 mg) in carbon tetrachloride (10 ml) and the mixture heated at reflux whilst irradiating with a 60 W tungsten lamp for 4 hours. The mixture was evaporated in vacuo, the solid residue dissolved in acetonitrile (5 ml) then added dropwise to a solution of N-methyl morpholine-N-oxide (0.2 g) in acetonitrile (10 ml) containing 4 Å sieves. The reaction mixture was stirred for 16 h at room temperature, filtered, the solvent removed in vacuo and the residue purified by FCC eluting with ether-hexane (2:1) to give the title compound as a white solid (56 mg) m.p. 174–175°.

T.l.c. (SiO$_2$) Ether Rf 0.5.

INTERMEDIATE 59

5-Hydroxymethyl-benzofuran-7-carbaldehyde

A mixture of 5-bromo-benzofuran-7-carbaldehyde (2.02 g), hydroxymethyltributyltin (4.29 g) and tetrakis (triphenylphosphine palladium (O) (1.03 g) in dry 1,4-dioxan (8 ml) was heated at reflux for 18 h. A further portion of catalyst (203 mg) was added and heating continued for 4 h. The reaction mixture was allowed to cool, and the solution was purified by FCC eluted with hexane:ethyl acetate (1:1) to give the title compound as yellow oil (0.95 g).

T.l.c. SiO2 (hexane:ethyl acetate 1:2), Rf 0.31.

EXAMPLE 1

[5-(5-Methyl-tetrazol-1-yl)-benzofuran-7-ylmethyl]-(2S-phenyl-piperidin-3S-yl)-amine dihydrochloride A solution of 3S-amino-2S-phenyl-piperidine (53 mg), 5-(5-methyl-tetrazol-1-yl)-benzofuran-7-carbaldehyde (69 mg) and acetic acid (21 mg) in dichloromethane (10 ml) was treated with sodium triacetoxyborohydride (108 mg) and left to stir at room temperature for 2 h. 8% Sodium bicarbonate solution (5 ml) was added to the reaction mixture which was left to stir for 15 min. The two phases were separated, the aqueous phase was extracted with chloroform (10 ml), the combined organic phases were dried, filtered and the filtrate evaporated in vacuo to give a yellow oil. Purification by FCC eluted with dichloromethane:ethanol:ammonia (100:8:1) gave a clear oil (76 mg). The oil was re-dissolved in ethanol (8 ml), treated with ethereal hydrogen chloride, and the resultant solid was removed by filtration and dried in vacuo to give the title compound as a fine white powder (49 mg), m.p. 256–259.5°.

T.l.c. (SiO2) Dichloromethane:ethanol:ammonia (100:8:1) Rf 0.32.

Similarly prepared:

EXAMPLE 2

[5-(1-Methyl-1H-[1,2,3]triazol-5-yl)-benzofuran-7-ylmethyl]-(2S-phenyl-piperidin-3S-yl)-amine, dihydrochloride as a pale cream solid (0.14 g), m.p. 273–6°

T.l.c. (SiO2) Dichloromethane:ethanol:ammonia (100:10:1), Rf 0.41.

From 3S-amino-2S-phenyl-piperidine (0.09 g) and 5-(1-methyl-1H-[1,2,3]-triazol-5-yl)-benzofuran-7-carbaldehyde (0.11 g).

EXAMPLE 3

(2S-Phenyl-piperidine-3S-yl)-(5-tetrazol-1-yl-benzofuran-7-ylmethyl)-amine dihydrochloride as a white solid (50 mg) m.p. 251–255°

T.l.c. (SiO$_2$) Dichloromethane-ethanol-ammonia 100:8:1, Rf 0.35.

From 5-tetrazol-1-yl-benzofuran-7-carbaldehyde (50 mg) and 3S-amino-2S-phenyl-piperidine (82 mg).

EXAMPLE 4

(2S-Phenyl-piperidin-3S-yl)-[5-(2H-[1,2,3]triazol-4-yl)-benzofuran-7-ylmethyl]-amine trihydrochloride as a yellow solid (50 mg), m.p. 220° C.

T.l.c. Dichloromethane:ethanol:ammonia (100:8:1), Rf=0.08.

From 3S-amino-2S-phenylpiperidine (50 mg) and 5-(2H-[1,2,3]triazol-4-yl)-benzofuran-7-carbaldehyde (60 mg).

EXAMPLE 5

[5-(2-Methyl-2H-[1,2,4]triazol-3-yl)-benzofuran-7-ylmethyl]-[2S-phenyl-piperidin-3S-yl]-amine trihydrochloride as a yellow solid (56 mg), m.p. 240–245° C.

TIC (SiO2) dichloromethane:ethanol:ammonia (100:8:1), Rf 0.53.

From 3S-amino-2S-phenyl-piperidine (104 mg) and 5-(2-methyl-2H-[1,2,4]triazol-3-yl)-benzofuran-7-carbaldehyde (135 mg).

EXAMPLE 6

[5-(1-Methyl-1H-[1,2,3]triazol-4-yl)-benzofuran-7ylmethyl]-(2S-phenyl-piperidin-3S-yl)-amine trihydrochloride as a yellow solid (37 mg), m.p. 220–230° C.

T.l.c. (SiO2) dichloromethane:ethanol:ammonia (100:8:1), Rf 0.35.

From 3S-amino-2S-phenyl-piperidine (30 mg) and 5-(1-methyl-1H-[1,2,3]triazol-4-yl)-benzofuran-7-carbaldehyde (60 mg).

EXAMPLE 7 cis-[5-(4-Methanesulfonyl-phenyl)-benzofuran-7-ylmethyl]-(2-phenyl-piperidin-3-yl)amine dihydrochioride as a white powder (181 mg), m.p. 259–263°

T.l.c. (SiO2) Dichloromethane:ethanol:ammonia (100:8:1) Rf 0.27.

From 5(4-methanesulfonyl-phenyl)-benzofuran-7-carbaldehyde (274 mg) and cis-3-amino-2-phenyl-piperidine (166 mg).

EXAMPLE 8

[5-(1-Methyl-1H-tetrazol-5-yl)-benzofuran-7-ylmethyl]-(2S-phenyl-piperidin-3S-yl)-amine dihydrochloride as a white powder (80 mg), m.p. 253–255°

T.l.c. (SiO2) Dichloromethane:ethanol:ammonia (100:8:1), Rf 0.18.

From 3S-amino-2S-phenyl-piperidine (63 mg) and 5-(1-methyl-1H-tetrazol-5-yl)-benzofuran-7-carbaldehyde (76 mg).

EXAMPLE 9

(5-Phenyl-benzofuran-7-ylmethyl)-(2S-phenyl-piperidine-3S-yl)-amine dihydrochloride as a white powder (109 mg), m.p. >260° decomp.

T.l.c. (SiO2) Dichloromethane:ethanol:ammonia (100:8:1) Rf 0.50.

From 3S-amino-2S-phenyl-piperidine (140 mg) and, 5-phenyl-benzofuran-7-carbaldehyde (174 mg).

EXAMPLE 10

(2S-Phenyl-piperidine-3S-yl)-(5-[1,2,3]triazol-1-yl-benzofuran-7-ylmethyl)-amine dihydrochloride as a pale brown solid (48 mg), m.p. 259–262°

T.l.c. (SiO$_2$) Dichloromethane-ethanol-ammonia 100:8:1, Rf 0.28.

From 3S-amino-2S-phenyl-piperidine (58 mg) and 5-[1,2,3]triazol-1-yl-benzofuran-7-carbaldehyde (70 mg).

EXAMPLE 11

(2S-Phenyl-piperidin-3S-yl)-[5-(5-trifluoromethyl-tetrazol-1-yl)-benzofuran-7-yl-methyl]-amine dihydrochloride (55 mg), m.p. 228–231°

T.l.c. (SiO$_2$) Dichloromethane-ethanol-ammonia 100:8:1, Rf 0.50.

From 5(5-Trifluoromethyl-tetrazol-1-yl)-benzofuran-7-carbaldehyde (95 mg) and 3S-amino-2S-phenyl-piperidine (71 mg).

EXAMPLE 12

(2S-Phenyl-piperidin-3S-yl)-(5-[1,2,4]triazol-1-yl-benzofuran-7-ylmethyl)-amine trihydrochloride 1-[7-(2S-phenyl-piperidin-3S-yl amino-methyl)-benzofuran-5-yl]-bicarbamic acid di-tert-butyl ester (218 mg) in propan-2-ol (5 ml) was treated with propan-2-olic hydrogen chloride, and heated in a steam bath for 10 min. Solvent was removed in vacuo to give a yellow powder, which was re-dissolved in ethanol (6 ml), treated with 1,3,5-triazine (34 mg) and heated at reflux for 16 h. 8% Sodium bicarbonate solution (5 ml) was added to the reaction which was extracted with chloroform (2×20 ml). The combined organic phases were dried, filtered and the filtrate evaporated in vacuo to give a brown gum. Purification by FCC eluted with dichloromethane:ethanol:ammonia (100:8:1) gave an orange gum (36 mg). The gum was treated with ethereal hydrogen chloride and concentrated in vacuo to give a brown powder. Trituration with ethyl acetate, filtration and drying in vacuo gave the title compound as a brown powder (35 mg).

T.l.c. (SiO2) Dichloromethane:ethanol:ammonia (100:8:1) Rf 0.28.

1H Nmr (D20) δ ppm 2.1(m), 2H; 2.3(m), 1H; 2.55(m), 1H; 3.3(m), 1H; 3.7(m), 1H; 4.05(m), 1H; 4.54(AB.q,J=14), 2H; 4.94(d,J=4), 1H; 7.05(d,J=2.5), 1H; 7.2–7.5(m), 6H; 7.85(d, J=2), 1H; 8.04(d, J=2), 1H; 8.29(s), 1H; 8.9(s), 1H.

EXAMPLE 13

[5-(5-Methyl-tetrazol-1-yl)-benzofuran-7-ylmethyl]-[2S-(4-fluoro-phenyl)-piperidin-3S-yl]-amine dihydrochloride 2S-(4-Fluoro-phenyl)-piperidin-3S-ylamine-2R,3R-bis-(4-methyl-benzoyloxy)-succinate (607 mg) was partitioned between chloroform (20 ml) and 8% sodium bicarbonate solution (20 ml). The phases were separated, the aqueous phase re-extracted with chloroform (20 ml) and the combined, dried, organics concentrated in vacuo to give 2S-(4-fluoro-phenyl)-piperidin-3S-ylamine (142 mg) as a yellow oil. The oil was dissolved in dichloromethane (20 ml) with 5-(5-methyl-tetrazol-1-yl)-benzofuran-7-carbaldehyde (162 mg), acetic acid (47 mg) and sodium triacetoxyborohydride (236 mg), and stirred at room temperature for 16 h. 8% sodium bicarbonate solution (20 ml) was added and the reaction stirred for a further 0.5 h. The mixture was extracted with chloroform (25 ml) and the dried organics concentrated in vacuo. Purification by FCC eluted with dichloromethane-ethanol-ammonia (200:8:1) gave a clear oil which was dissolved in ethanol (10 ml), and treated with ethereal hydrogen chloride. The solvent was removed in vacuo to give a yellow powder. Recrystallisation from methanol gave the title compound as colorless crystals, m.p. 263–265°.

T.l.c. (SiO2) Dichloromethane-ethanol-ammonia (100:8:1), Rf 0.29.

EXAMPLE 14

[2S-(4-Fluoro-phenyl)-piperidin-3S-yl]-[5-(2-methyl-2H-pyrazol-3-yl)-benzofuran-7-ylmethyl]-amine trihydrochloride (186 mg), m.p. 227–229°

T.l.c. (SiO$_2$) Dichloromethane-ethanol-ammonia 100:8:1, Rf 0.43.

From 3S-amino-2S-(4-fluoro-phenyl)-piperidine (140 mg) and 5-(2-methyl-2H-pyrazol-3-yl)-benzofuran-7-carbaldehyde (163 mg).

EXAMPLE 15

5-(2,3-Dimethyl-3H-imidazol-4-yl)-benzofuran-7-ylmethyl]-(2S-phenyl-piperidin-3S-yl)-amine trihydrochloride (88 mg) m.p. 233–234°

T.l.c. (SiO$_2$) Dichloromethane-ethanol-ammonia 200:8:1, Rf 0.1.

From 3S-amino-2S-phenyl-piperidine (153 mg) and 5-(2,3dimethyl-3H-imidazol-4-yl)-benzofuran-7-carbaldehyde (210 mg).

EXAMPLE 16

[5-(3,5-Dimethyl-isoxazol-4-yl)-benzofuran-7-ylmethyl]-[2S-phenyl-piperidin-3S-yl]-amine dihydrochloride (60 mg), m.p. 245° (decomp.)

T.l.c. (SiO$_2$) Dichloromethane-ethanol-ammonia 100:8:1, Rf 0.63.

From 3S-amino-2S-phenyl-piperidine (160 mg) and 5-(3,5-dimethyl-isoxazol-4-yl)-benzofuran-7-carbaldehyde (153 mg).

EXAMPLE 17

[5-(1-Methyl-1H-imidazol-2-yl)-benzofuran-7-ylmethyl]-(2S-phenyl-piperidin-3S-yl)-amine trihydrochloride (515 mg), m.p. 220°

T.l.c. (SiO$_2$) Dichloromethane-ethanol-ammonia 100:8:1, Rf 0.4.

From 3S-amino-2S-phenyl-piperidine (351 mg) and 5-(1-methyl-1H-imidazol-2-yl)-benzofuran-7-carbaldehyde (450 mg).

EXAMPLE 18

[5-(2-Methyl-2H-pyrazol-3-yl)-benzofuran-7-ylmethyl]-(2S-phenyl-piperidin-3S-yl)-amine trihydrochloride (850 mg), m.p. 235–238°

T.l.c. (SiO$_2$) Dichloromethane-ethanol-ammonia 100:8:1, Rf 0.25.

From 3S-amino-2S-phenyl-piperidine (551 mg) and 5-(2-methyl-2H-pyrazol-3-yl)-benzofuran-7-carbaldehyde (708 mg).

EXAMPLE 19

(2S-Phenyl-piperidin-3S-yl)-[5-(1H-pyrazol-4-yl)-benzofuran-7-ylmethyl]-amine trihydrochloride (204 mg), m.p. 240° (decomp.)

T.l.c. (SiO$_2$) Dichloromethane-ethanol-ammonia 100:8:1, Rf 0.19.

From 3S-amino-2S-phenyl-piperidine (156 mg) and 5-(1H-pyrazol-4-yl)-benzofuran-7-carbaldehyde (189 mg).

EXAMPLE 20 cis-(2-Phenyl-piperidin-3-yl)-(5-pyrazin-2-yl-benzofuran-7-ylmethyl)-amine dihydrochloride (217 mg), m.p. 247–252°

T.l.c. (SiO$_2$) Dichloromethane-ethanol-ammonia 100:8:1, Rf 0.23.

From cis-3-amino-2-phenyl-piperidine (279 mg) and 5-pyrazin-2-yl-benzofuran-7-carbaldehyde (314 mg).

EXAMPLE 21

4-{7-[(2S-Phenyl-piperdin-3S-ylamino)-methyl]-benzofuran-5-yl}-pyridine-2-carboxylic acid dimethylamide trihydrochloride (41 mg), m.p. 274° decomp.

T.l.c. (SiO$_2$) Dichloromethane-ethanol-ammonia 200:8:1, Rf 0.14,.

From 4-(7-formyl-benzofuran-5-yl)-pyridine-2-carboxylic acid dimethylamide (89 mg) and 3S-amino-2S-phenyl-piperidine (55 mg).

EXAMPLE 22

4{-7-[(2S-Phenyl-piperidin-3S-ylamino)-methyl]-benzofuran-5-yl}-pyridine-2-carbonitrile dihydrochloride (61 mg), m.p. 259° (decomp.)

T.l.c. (SiO$_2$) Dichloromethane-ethanol-ammonia 100:8:1, Rf 0.33.

From 3S-amino-2S-phenyl-piperidine (95 mg) and 5-(pyridine-2-carbonitrile)-benzofuran-7-carbaldehyde (139 mg).

EXAMPLE 23

(2S-Phenyl-piperidin-3S-yl)-(5-pyridin-4-ylmethyl-benzofuran-7-ylmethyl)-amine trihydrochloride (113 mg), m.p. 253–255°

T.l.c. (SiO$_2$) Dichloromethane-ethanol-ammonia 100:8:1, Rf 0.24.

From 3S-amino-2S-phenyl-piperidine (130 mg) and 5-pyridin-4-ylmethyl-benzofuran-7-carbaldehyde (159 mg).

EXAMPLE 24

[5-(2-Methyl-pyridin-4-yl)-benzofuran-7-ylmethyl]-(2S-phenyl-piperidin-3S-yl)-amine trihydrochloride (103 mg), m.p. 235–237°

T.l.c. (SiO$_2$) Dichloromethane-ethanol-ammonia 100:8:1, Rf 0.22.

From 3S-amino-2S-phenyl-piperidine (84 mg) and 5-(2-methyl-pyridin-4-yl)-benzofuran-7-carbaldehyde (64 mg).

EXAMPLE 25

[6-Methoxy-5-pyridin-4-ylbenzofuran-7-ylmethyl]-(2S-phenyl-piperidin-3S-yl)-amine trihydrochloride (250 mg), m.p. >200° (decomp.)

T.l.c. (SiO$_2$) Dichloromethane-ethanol-ammonia 100:8:1, Rf 0.4

From 3S-amino-2S-phenyl-piperidine (190 mg) and 6-methoxy-5-pyridin-4-ylbenzofuran-7-carbaldehyde (230 mg).

EXAMPLE 26

[6-Methoxy-5-(2-methyl-2H-pyrazol-3-yl)-benzofuran-7-ylmethyl]-(2S-phenyl-piperidin-3S-yl)-amine, trihydrochloride (0.115 g), m.p. 230–240°

T.l.c. (SiO$_2$) Dichloromethane-ethanol-ammonia 100:8:1, Rf 0.32.

From 3S-amino-2S-phenyl-piperidine (0.18 g) and 6-methoxy-5-(2-methyl-2H-pyrazol-3-yl)-benzofuran-7-carbaldehyde (0.215 g).

EXAMPLE 27

(5-Isoxazol-4-yl-benzofuran-7-ylmethyl)-(2S-phenyl-piperidin-3S-yl)-amine dihydrochloride (81 mg), m.p. >280° (decomp.)

T.l.c. (SiO$_2$) Dichloromethane-ethanol-ammonia 100:8:1, Rf 0.24.

From 3S-amino-2S-phenyl-piperidine (70 mg) and 5-isoxazol-4-yl-benzofuran-7-carbaldehyde (80 mg).

EXAMPLE 28

(2S-Phenyl-piperidin-3S-yl)-(5-tetrazol-2-ylmethyl-benzofuran-7-yl-methyl)-amine dihydrochloride (354 mg). m.p. 224–227°

T.l.c. (SiO$_2$) Dichloromethane-ethanol-ammonia 100:8:1, Rf 0.33.

From 5-tetrazol-2-ylmethyl-benzofuran-7-carbaldehyde (314 mg) and 3S-amino-2S-phenyl-piperidine (268 mg)

EXAMPLE 29

(2S-Phenyl-piperidin-3S-yl)-(5-tetrazol-1-ylmethyl-benzofuran-7-yl-methyl)-amine dihydrochloride (136 mg). m.p. >290° (decomp.)

T.l.c. (SiO$_2$) Dichloromethane-ethanol-ammonia 100:8:1, Rf 0.44.

From 3S-amino-2S-phenyl-piperidine (116 mg) and 5-tetrazol-1-yl-methylbenzofuran-7-carbaldehyde (131 mg).

EXAMPLE 30

[5-(3,5-Dimethyl-1H-pyrazol-4-yl)-benzofuran-7-ylmethyl]-(2S-phenyl-piperidin-3S-yl)amine trihydrochloride (12 mg), m.p. 267° C.

T.l.c. (SiO$_2$) Dichloromethane-ethanol-ammonia 100:8:1, Rf 0.4.

From 3S-amino-2S-phenyl-piperidine (30 mg) and 5-(3,5-dimethyl-1H-pyrazol-4-yl)-benzofuran-7-carbaldehyde (40 mg).

EXAMPLE 31

[5-(3-Methyl-3H-imidazol-4-yl)-benzofuran-7-ylmethyl]-(2S-phenyl-piperidin-3S-yl)-amine trihydrochloride (28 mg) m.p. 221°

T.l.c. (SiO$_2$) Dichloromethane-ethanol-ammonia 200:8:1, Rf 0.3

From 3S-amino-2S-phenyl-piperidine (52 mg) and 5-(3-methyl-3H-imidazol-4-yl)-benzofuran-7-carbaidehyde (74 mg).

EXAMPLE 32

(5-Oxazol-2-yl-benzofuran-7-ylmethyl)-(2S-Phenyl-piperidine-3S-yl)-amine dihydrochloride (104 mg). m.p. 249–252°

T.l.c. (SiO$_2$) Dichloromethane-ethanol-ammonia 100:8:1, Rf 0.5.

From 3S-amino-2S-phenyl-piperidine (180 mg) and 5-oxazol-2-yl-benzofuran-7-carbaldehyde (0.2 g).

EXAMPLE 33 cis-(2-Phenyl-piperidin-3-yl)-(5-thiazol-2-yl-benzofuran-7-yl-methyl)-amine trihydrochloride (140 mg) m.p. 182–188°

T.l.c. (SiO$_2$) Dichloromethane-ethanol-ammonia 100:8:1, Rf 0.33.

From 5-Thiazol-2-yl-benzofuran-7-carbaldehyde (111 mg) and cis-3-amino-2-phenyl-piperidine (86 mg).

EXAMPLE 34 cis-(2-Phenyl-piperidin-3-yl)-(5-pyridin-3-yl-benzofuran-7-ylmethyl)-amine, trihydrochloride (123 mg), m.p. 184–188°

T.l.c. dichloromethane-ethanol-ammonia 100:8:1, Rf 0.32

5-(3-Pyridyl)-benzofuran-7-carboxaldehyde (70 mg) and cis-3-amino-2-phenyl-piperidine (53 mg)

EXAMPLE 35

(5-Pyrazol-1-yl-benzofuran-7-ylmethyl)-(2S-phenyl-piperidin-3S-yl)-amine trihydrochloride A stirred solution of 1-(7-[1,3]dioxan-2-yl-benzofuran-5-yl)-1H-pyrazole (110 mg) in hydrochloric acid (2M; 5 ml) and tetrahydrofuran (5 ml) was heated at 80° for 20 min. The solution was cooled, basified with 1M sodium carbonate solution and extracted with dichloromethane (2×20 ml). The extracts were washed with water (20 ml), dried, and evaporated to dryness to give a pale yellow solid (73 mg). A solution of this solid, 3S-amino-2S-phenyl-piperidine (77 mg) and sodium triacetoxyborohydride (98 mg) in dichloromethane (10 ml) was stirred for 16 h at room temperature. The reaction mixture was diluted with 8% sodium bicarbonate solution (25 ml) and extracted with dichloromethane (2×20 ml). The combined, dried, organics were concentrated in vacuo and the residual oil (130 mg) purified by FCC eluted with dichloromethane-ethanol-ammonia (100:8:1). The clear oil was dissolved in ethanol (5 ml) and treated with ethereal hydrogen chloride. The solvent was removed in vacuo and the residue was crystallized from methanol-ethyl acetate to give the title compound (41 mg), m.p. 266–268°.

T.l.c. (SiO$_2$) Dichloromethane-ethanol-ammonia 100:8:1, Rf 0.3.

Similarly prepared:

EXAMPLE 36

(5-Imidazol-1yl-benzofuran-7-ylmethyl)-(2S-phenyl-piperidin-3S-yl)-amine trihydrochloride (45 mg), m.p. 203–208°

Mass. Spec. MH$^+$373

From 1-(7-[1,3]dioxan-2-yl-benzofuran-5-yl-1H-imidazole (270 mg) and 3S-amino-2S-phenyl-piperidine (105 mg).

EXAMPLE 37 cis-2-Phenyl-piperidin-3-yl)-(5-pyridin-4-yl-benzofuran-7-ylmethyl)-amine, trihydrochloride A solution of cis-3-[(5-bromobenzofuran-7-ylmethyl)tert-butoxycarbonyl-amino]-2-phenyl-piperidine-1-carboxylic acid tert-butyl ester (413 mg), 4-pyridylboronic acid (109 mg) and tetrakis (triphenylphosphine)palladium (O) (40 mg) in dimethoxyethane (10 ml) and 8% sodium bicarbonate (4 ml) was heated at reflux for 2 h. The reaction mixture was allowed to cool, solvent was removed in vacuo, and the residue was partitioned between water (20 ml) and chloroform (30 ml). The organic phase was dried, filtered and the filtrate evaporated in vacuo to give a brown foam (454 mg). The carbamate (454 mg) in dichloromethane (20 ml) was treated with trifluoroacetic acid (7 ml) and left to stir at room temperature for 18 h. A further portion of trifluoroacetic acid (2 ml) was added and the reaction mixture left to stir for 3 h. Water (15 ml) was added, and the mixture basified with 2N sodium hydroxide. The organic phase was dried, filtered and the filtrate evaporated in vacuo to give a brown oil. Purification by FCC eluting with dichloromethane-ethanol-ammonia (100:8:1) gave a yellow oil (218 mg). The oil was redissolved in ethanol (5 ml), treated with ethereal hydrogen chloride, and solvent removed in vacuo. Trituration with ether gave the title compound as a pale green powder (180 mg), m.p. >230° (decomp.).

T.l.c. dichloromethane-ethanol-ammonia 100:8:1, Rf 0.23

EXAMPLE 38 cis-(2-Phenyl-piperidin-3-yl)-(5-furan-3-yl-benzofuran-7-ylmethyl)-amine, dihydrochloride cis-3-[(5-Furan-3-ylbenzofuran-7-ylmethyl)tert-butoxycarbonyl-amino)-piperidine-1-carboxylic acid tert-butyl ester (370 mg) in methanol (5 ml) and 5N hydrochloric acid (7 ml) was left to stir at room temperature for 48 h. The reaction mixture was neutralized with 2N sodium hydroxide, and extracted with chloroform (2×20 ml). The combined organic phases were dried, filtered and the filtrate evaporated in vacuo to give a yellow gum (350 mg). The gum was redissolved in dichloromethane (15 ml), treated with trifluoroacetic acid (5 ml) and left to stand at room temperature for 24 h. The reaction mixture was neutralized with 2N sodium hydroxide, diluted with water (10 ml) and extrated with chloroform (2×20 ml). The combined organic phase was dried, filtered and the filtrate evaporated in vacuo to give a brown oil. The oil was redissolved in ethanol (10 ml), treated with ethereal hydrochloric acid and solvent removed in vacuo. Trituration in ether gave a brown solid which was recrystallised from isopropanol to give a fawn powder (153 mg), m.p. 236–237°.

T.l.c. dichloromethane-ethanol-ammonia 100:8:1, Rf 0.58

EXAMPLE 39 cis-(2-Phenyl-piperidin-3-yl)-(5-pyrimidin-5-yl-benzofuran-7-ylmethyl)-amine, trihydrochloride A mixture of cis-2-phenyl-3-[(5-pyrimidin-5-yl-benzofuran-7-ylmethyl)-amino]-piperidine-1-carboxylic acid tert-butyl ester (90 mg) and cis-2-phenyl-3-[(5-pyrimidin-5-yl-benzofuran-7-ylmethyl)tert-butoxycarbonyl-amino]-piperidine-1-carboxylic acid tert-butyl ester (190 mg) in methanol (7 ml) and 5N hydrochloric acid (7 ml) was left to stir at room temperature for 65 h. The reaction mixture was concentrated in vacuo, basified with 2N sodium hydroxide and extracted with ethyl acetate (2×20 ml). The organic phases were washed with brine (30 ml), combined, dried, filtered and the filtrate evaporated in vacuo to give a brown gum (180 mg). Purification by FCC eluting with dichloromethane-ethanol-ammonia (100:8:1) gave a yellow oil (103 mg). The oil was redissolved in ethanol (15 ml), treated with ethereal hydrogen chloride and solvent removed in vacuo. Trituration with propan-2-ol gave the title compound as a pale yellow powder (110 mg), m.p. 218° (decomp.).

T.l.c. dichloromethane-ethanol-ammonia 100:8:1, Rf 0.22

Similarly prepared:

EXAMPLE 40 cis-(2-Phenyl-piperidin-3-yl)-(5-pyridin-2-yl-benzofuran-7-ylmethyl)-amine, trihydrochloride
(151 mg), m.p. 220–224°

T.l.c. dichloromethane-ethanol-ammonia 100:8:1, Rf 0.29.

From cis-3-[(5-pyridin-2-yl-benzofuran-7-ylmethyl)tert-butoxycarbonyl-amino]-piperidine-1-carboxylic acid tert-butyl ester (280 mg).

Biological Data

As mentioned hereinbefore, compounds of the invention have been shown to inhibit radiation-induced emesis in the ferret at a dose of 0.3–3 mg/kg s.c. using the test as described hereinbefore. More specifically the compound of Example 1, [5-(5-Methyl-tetrazol-1-yl)-benzofuran-7-ylmethyl]-(2S-phenyl-piperidin-3S-yl)-amine dihydrochloride, inhibited radiation-induced emesis in the ferret at a dose of 0.3 mg/kg s.c.

No apparent adverse or toxic effects were observed during the above in vivo tests due to the administration of the compounds of the invention.

PHARMACY EXAMPLES

Example A

Sterile Formulation

|  | mg/ml |
|---|---|
| Compound of formula (I) dihydrochloride | 0.3 mg |
| Sodium Chloride USP | 6.0 mg |
| Sodium Acetate USP | 2.6 mg |
| Acetic Acid | 1.1 mg |
| Water for Injection USP | qs to 1 ml |

The components are dissolved in a portion of the water for injection and the solution made up to final volume.

The solution may be packaged for injection, for example by filling and sealing in ampoules, vials or syringes. The ampoules, vials or syringes may be aseptically filled and/or terminally sterilised by, for example, autoclaving at 121° C.

Further sterile formulations may be prepared, in a similar manner, containing 6 mg of the compound of formula (I) dihydrochloride.

TABLETS FOR ORAL ADMINISTRATION

Tablets may be prepared by the normal methods such as direct compression or wet granulation.

The tablets may be film coated with suitable film forming materials, such as Opadry White, type YS-1-7027, using standard techniques. Alternatively the tablets may be sugar coated.

Example B

Direct Compression

| Tablet | mg/Tablet |
|---|---|
| Compound of formula (I), dihydrochloride | 0.6 mg |
| Magnesium Stearate | 0.75 mg |
| Avicel PH102 | qs 150.00 mg |

The compound of formula (I) dihydrochloride is passed through a 30 mesh sieve and blended with Avicel PH102 and magnesium stearate. The resultant mix is compressed into tablets using a suitable tablet machine fitted with 9/32" diameter punches.

Tablets of other strengths, containing for example 2.4, 6.0 or 12.0 mg/tablet of the compound of formula (I) dihydrochloride, may be prepared in a similar manner.

Example C

Wet Granulation

A formulation as described in Example B may be used. The compound of formula (I) dihydrochloride is dissolved in a suitable volume of granulating solution (purified water or 10% PVP K29/32 in water). After drying, the granules are screened, for example through 20 mesh screen, and blended with magnesium stearate. The granules are then compressed into tablets as described in Example B.

Tablets of other strengths, such as those described in Example B, may be prepared in a similar manner.

Example D
Suppository

| | |
|---|---|
| Compound of formula (I), dihydrochloride | 10.0 mg |
| Witepsol W32, hard fat | qs 2000 mg |

Blend micronized drug in a portion of the melted Witepsol W32 at approximately 36° C. for approximately 15 minutes in a high speed mixer. Incorporate the homogenized slurry into the remaining portion of the melted Witepsol W32 and blend at approximately 36° C. until satisfactory dispersion is achieved. Fill molds with 2000 mg formulation, to provide 10 mg/suppository of compound of formula (I) dihydrochloride.

Example E
Capsule

| | mg/capsule |
|---|---|
| Compound of formula (I), dihydrochloride | 12.0 mg |
| Polyethylene glycol | 92.89 mg |
| Propylene glycol | qs 200 mg |

Blend together polyethylene glycol and propylene glycol using heat as necessary. Stir until homogeneous. Add micronised compound of formula (I) dihydrochloride to blend. Mix until homogenous. Fill into an appropriate gelatin mass to give soft gelatin capsules containing 200 mg of the formulation, to provide 12 mg/capsule of compound of formula (I). Additional strengths, e.g. 0.5, 2.0 and 5.0 mg/capsule of compound of formula (I) dihydrochloride, may be prepared in a similar manner.

Example F
Oral Syrup

| | mg/ml |
|---|---|
| Compound of formula (I), dihydrochloride | 6.0 mg |
| Sucrose | 200 mg |
| Methylparaben | 1.2 mg |
| Propylparaben | 0.15 mg |
| Flavouring | 1.5 mg |
| Citric Acid | 0.1 mg |
| Purified Water | qs 1 ml |

Dissolve the parabens in a small portion of the water that has been heated to approximately 90° C. Add the paraben solution to a large portion of the remaining water with mixing. Add and dissolve the other components. Bring the formulation to final volume and mix until homogenous. Fill the formulation into a containing, such as a unit dose cup or a bottle for multiple-dose use.

Example G
Transdermal System

| | |
|---|---|
| Compound of formula (I), dihydrochloride | 5% (of compound of formula (I)) |
| Silicone fluid | 90% |
| Colloidal silicone dioxide | 5% |

The silicone fluid and drug are mixed together and the colloidal silicone dioxide is added to increase the viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene or polyvinyl acetate) or polyurethane, and an impermeable backing membrane of a polyester multilaminate.

Example H
Lyophilized Product

| | |
|---|---|
| Compound of formula (I), dihydrochloride | 6.0 mg |
| Mannitol | 50.0 mg |
| Acetate buffer | 8.2 mg |
| Water for injection | qs 1 ml |

Dissolve components in a portion of the water for injection. Make formulation up to final volume and mix until homogenous. Filter formulation through a sterilising filter and fill into glass vials. Lyophilize and seal vials. Reconstitute with appropriate solvent prior to use.

Example I
Hard Gelatin Capsule

| | |
|---|---|
| Compound of formula (I) dihydrochloride | 12.00 mg |
| Lactose | 80.00 mg |
| Magnesium Stearate | 0.75 mg |
| Avicel pH 102 | qs 150.00 mg |

The compound of formula (I) dihydrochloride is passed through a 30 mesh sieve and blended with lactose, Avicel pH 102 and magnesium stearate. The resultant mix is encapsulated into hard gelatin capsules using a suitable capsule machine.

Capsules of other strengths can be similarly made to provide 0.5, 2 and 5 mg/capsule of compound of formula (I).

We claim:
1. A compound of formula (I)

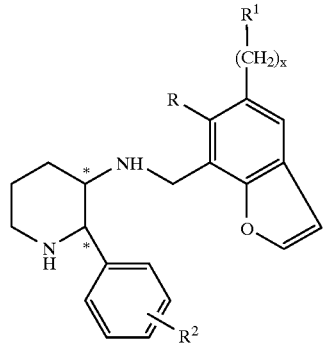

(I)

wherein

R represents a hydrogen atom or a $C_{1-4}$alkoxy group; $R^1$ is selected from phenyl, optionally substituted by a group $-(CH_2)_n CONR^3 R^4$ or $S(O)_m R^3$; or a 5- or 6-membered aromatic heterocycle containing 1, 2, 3, or 4 heteroatoms selected from oxygen, nitrogen or sulphur, optionally substituted by a $C_{1-4}$alkyl, trifluoromethyl or cyano group or a group $-(CH_2)_n CONR^3 R^4$;

$R^2$ represents a hydrogen or halogen atom;

$R^3$ and $R^4$ independently represent hydrogen or $C_{1-4}$alkyl;

n represents zero, 1 or 2;

m represents zero 1 or 2;

x represents zero or 1;

or a pharmaceutically acceptable salt or solvate thereof.

2. A compound according to claim 1 wherein

R represents a hydrogen atom; $R^1$ is selected from phenyl, optionally substituted by a group —$(CH_2)_nCONR^3 R^4$ or $S(O)_mR^3$; or a 5- or 6-membered aromatic heterocycle containing 1, 2, 3, or 4 heteroatoms selected from oxygen, nitrogen or sulphur, optionally substituted by a $C_{1-4}$alkyl group;

$R^2$ represents a hydrogen atom;

$R^3$ and $R^4$ independently represent hydrogen or $C_{1-4}$alkyl;

n represents zero, 1 or 2;

m represents zero 1 or 2; and x represents zero.

3. A compound according to claim 1 wherein $R^1$ represents pyrimidine, furan, pyridine, imidazole, tetrazole, pyrazole, pyrazine, oxazole, thiazole, triazole, isoxazole, 1,2,4-oxadiazole or 1,3,4-oxadiazole.

4. A compound according to claim 1 wherein R represents hydrogen.

5. A compound according to claim 1 wherein $R^2$ represents hydrogen.

6. A compound according to claim 1 wherein x represents zero.

7. A compound according to claim 1 wherein $R^1$ represents 1,2,3-triazole or 1,2,4-triazole.

8. A compound according to claim 1 wherein $R^1$ represents tetrazole.

9. The compound which is [5-(5-methyl-tetrazol-l-yl)-benzofuran-7-ylmethyl]-(2S-phenyl-piperidin-3S-yl)-amine or a pharmaceutically acceptable salt or solvate thereof.

10. A pharmaceutical composition comprising a therapeutically effective amount of a compound according to claim 1 or a pharmaceutically acceptable salt or solvate thereof, together with a pharmaceutically acceptable carrier.

11. A process for preparing a compound of formula (I) as defined in claim 1, or a pharmaceutically acceptable salt or solvate thereof which comprises:

(A) reacting a compound of formula (II)

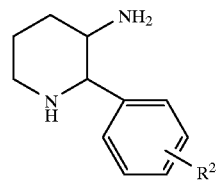
(II)

with a compound of formula (III)

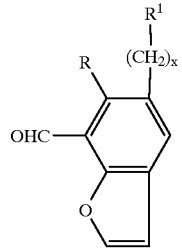
(III)

followed by reduction: or (B) reacting a compound of formula (VIII)

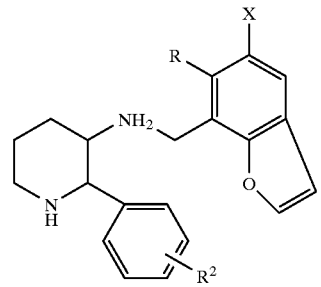
(VIII)

(where X is a suitable leaving group) or a protected derivative thereof, with a compound of formula (IX)

$R^1$—$(CH_2)_x$—Y  (IX)

(where Y represents $B(OH)_2$, or $Sn(alkyl)_3$) followed by deprotection where necessary.

12. A method for treating $NK^1$ receptor-mediated pain, inflammation, allergy, CNS disorder, GI disorder or emesis in a mammal, comprising administering to said mammal in need thereof an $NK_1$ antagonistic effective amount of a compound according to claim 1 or a pharmaceutically acceptable salt or solvate thereof.

13. The method of claim 12 wherein the $NK_1$ receptor-mediated CNS disorder is depression.

* * * * *